United States Patent
Webster et al.

(10) Patent No.: US 9,605,349 B2
(45) Date of Patent: Mar. 28, 2017

(54) DECREASING BACTERIAL RESPONSES ON NANO-MODIFIED TITANIUM

(71) Applicant: Howmedica Osteonics Corp., Mahwah, NJ (US)

(72) Inventors: Thomas J. Webster, Barrington, RI (US); Godofredo R. Dimaano, South Plainfield, NJ (US); Kevor Shane Tenhuisen, Bloomingdale, NJ (US); Gene Kulesha, Ringwood, NJ (US); John Muth, Mahwah, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 30 days.

(21) Appl. No.: 14/570,374

(22) Filed: Dec. 15, 2014

(65) Prior Publication Data
US 2016/0166391 A1   Jun. 16, 2016

(51) Int. Cl.
*A61F 2/30* (2006.01)
*C23F 1/00* (2006.01)
*C23F 1/26* (2006.01)
*A61L 31/02* (2006.01)
*A61L 27/06* (2006.01)

(52) U.S. Cl.
CPC ........... *C23F 1/26* (2013.01); *A61L 27/06* (2013.01); *A61L 31/022* (2013.01); *A61F 2002/3084* (2013.01); *A61L 2400/12* (2013.01); *A61L 2400/18* (2013.01)

(58) Field of Classification Search
None
See application file for complete search history.

(56) References Cited

U.S. PATENT DOCUMENTS

| | | | |
|---|---|---|---|
| 5,219,361 A | 6/1993 | von Recum et al. |
| 8,221,499 B2 | 7/2012 | Lazzara et al. |
| 8,221,639 B2 | 7/2012 | Towse et al. |
| 8,251,700 B2 | 8/2012 | Robb et al. |
| 8,303,830 B2 | 11/2012 | Tong et al. |

(Continued)

FOREIGN PATENT DOCUMENTS

WO   2006/029708 A1   3/2006

OTHER PUBLICATIONS

Kilpadi et al (Cleaning and Heat-treatment Effects on Unalloyed Titanium Implant Surfaces; The International Journal of Oral & maxillofacial Implants; 2000; vol. 15, No. 2, p. 219-230.*

(Continued)

*Primary Examiner* — Shamim Ahmed
(74) *Attorney, Agent, or Firm* — Lerner, David, Littenberg, Krumholz & Mentlik, LLP

(57) ABSTRACT

Methods of manufacturing produce metal implants having nano-modified surfaces that contain antimicrobial properties. The methods may include immersing the implant in an acid, rinsing the acid-treated implant in an aqueous cleaner, and thereafter heating the rinsed implant. The nano-modified implants described herein may contain an increased surface roughness; surface features with increased width or height; and/or decreased surface energy. The implants that result from these methods contain a nano-modified surface that is resistant to microbial cell adhesion and ultimately reduce biomaterials-related infections at the implant site.

12 Claims, 56 Drawing Sheets

Growth of *Staphyloccocus epidermidis* on Non-Porous Titanium Implants Treated with 5N Nitric Acid

(56) References Cited

U.S. PATENT DOCUMENTS

| | | | |
|---|---|---|---|
| 8,545,559 B2 | 10/2013 | Bandyopadhyay et al. | |
| 8,821,586 B2 * | 9/2014 | Bjursten | A61F 2/28 623/11.11 |
| 2004/0167633 A1 * | 8/2004 | Wen | A61F 2/30767 623/23.57 |
| 2009/0326674 A1 * | 12/2009 | Liu | A61F 2/30767 623/23.55 |
| 2010/0168841 A1 * | 7/2010 | Furst | A61L 27/047 623/1.42 |
| 2012/0074098 A1 * | 3/2012 | Nary Filho | A61C 8/0015 216/53 |

OTHER PUBLICATIONS

Puckett et al., "The relationship between the nanostructure of titanium surface and bacterial attachment", Biomaterials 31:706-713 (2010).

Taylor et al., "Reducing infections through nanotechnology and nanoparticles", International Joural of Nanomedicine 6:1463-1473 (2011).

ASTM International, "Standard Specification for Chemical Passivation Treatments for Staninless Steel Parts", Designation:A967/A967M-13.

ASTM International, "Standard Guide for Descaling and Cleaning Titanium and Titanium Alloy Surfaces", Designation: B600-11.

ASTM International, "Standard Practice for Surface Preparation and Marking of Metallic Surgical Implants", Designation:F86-13.

\* cited by examiner

Growth of *Staphyloccocus epidermidis* on Non-Porous Titanium Implants Treated with 1N Nitric Acid Growth of *Staphyloccocus epidermidis* on Non-Porous Titanium Implants Treated with 5N Nitric Acid Growth of *Staphyloccocus epidermidis* on Porous Titanium Implants Treated with 1N Nitric Acid Growth of *Staphyloccocus epidermidis* on Porous Titanium Implants Treated with 5N Nitric Acid Growth of *Staphyloccocus aureus* on Non-Porous Titanium Implants Treated with 5N Nitric Acid Growth of *Staphyloccocus aureus* on Non-Porous Titanium Implants Treated with 10N Nitric Acid Growth of *Staphyloccocus aureus* on Porous Titanium Implants Treated with 5N Nitric Acid Growth of *Staphyloccocus aureus* on Porous Titanium Implants Treated with 10N Nitric Acid

FIG. 18
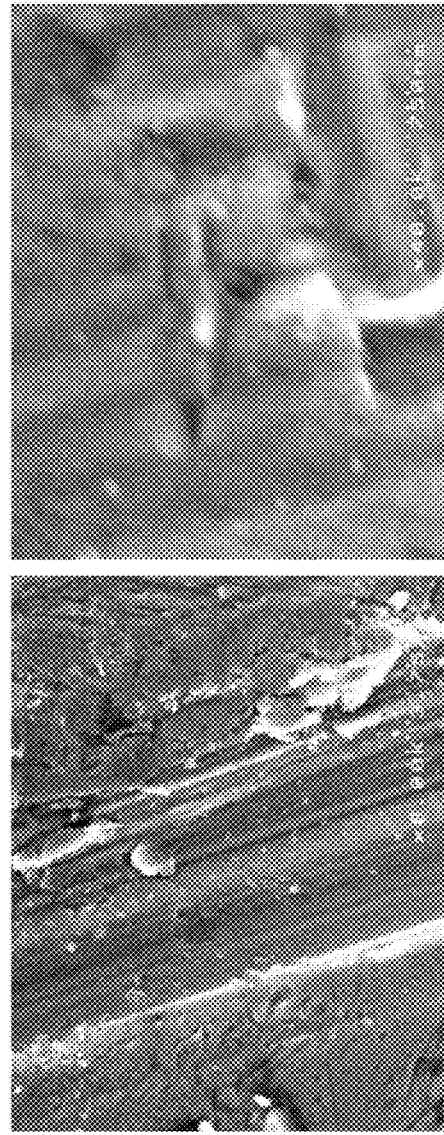
Non-Porous 5M HNO3, 30 minutes, 200°C
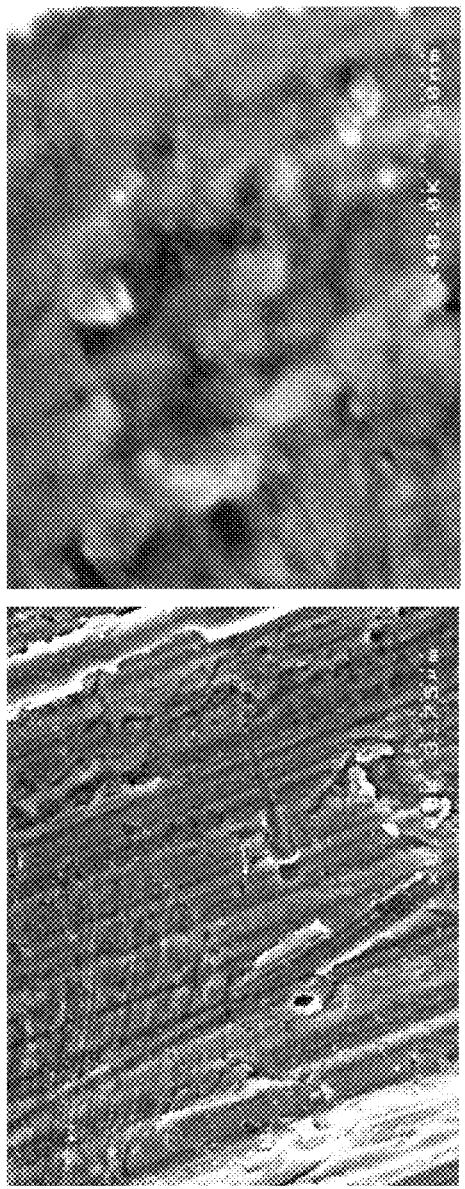
Non-Porous 5M HNO3, 30 minutes, 600°C

FIG. 25
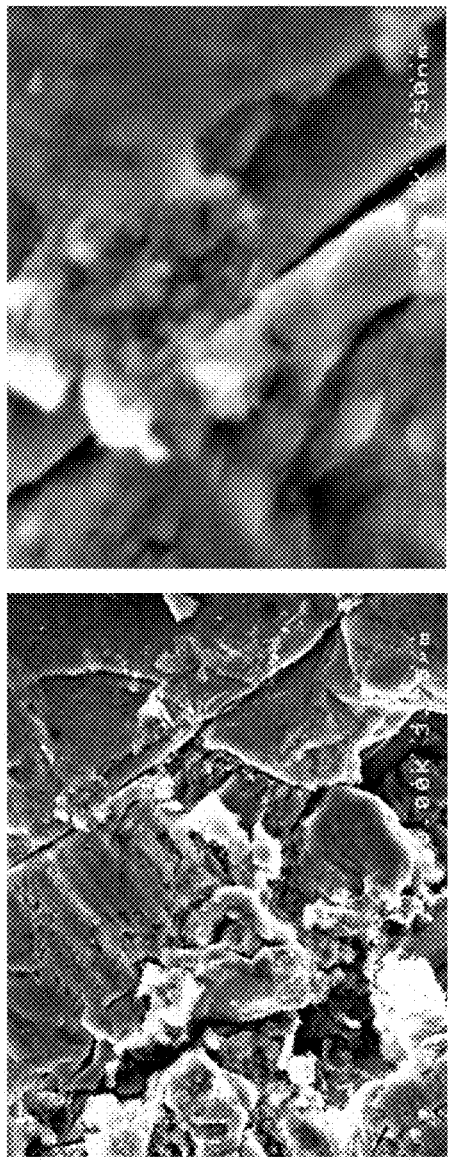

Porous 10M HNO3, 60 minutes, 600°C

DECREASING BACTERIAL RESPONSES ON NANO-MODIFIED TITANIUM

BACKGROUND OF THE INVENTION

It has become common to treat a variety of medical conditions by introducing an implantable medical device partly or completely into the human body. For example, orthopedic devices are commonly inserted into joints such as the knee, spine, shoulder and the like. Additional orthopedic devices are often implanted adjacent bone such as metal plates during fracture repair and spinal rods for the re-alignment of the spine. Many other implants are used for implantation into the esophagus, trachea, colon, biliary tract, urinary tract, vascular system or other locations within a human or even a veterinarian patient.

One disadvantage associated with implantable medical devices, especially titanium and titanium alloy devices, is microbial adhesion to titanium surfaces. Microbial adhesion occurs when unwanted microorganisms adhere to the orthopedic implant either during implantation or afterwards. Microbial adhesion to the surface of an implant device that eventually lead to biomaterials-related infections is a well-recognized complication of implant materials and devices. Once adhesion has occurred, proliferation of the microbial agents leads to the development of a biofilm, which is unsusceptible to most therapeutic agents at achievable concentrations. Thus, the course of microbial infection involves three major steps: microbial adhesion; microbial proliferation; and formation of a bacterial bio-film.

Typically metal implants are passivated by a known process. First, the metals to be passivated are washed using a detergent for 40 minutes in an ultrasonic bath at 65 degrees C., followed by de-ionized water rinsing in an ultrasonic bath at 65 degrees C. The metals are then passivated by immersing them in 30% Nitric acid solution at room temperature or a temperature below 100° for 30 minutes. After the passivation, the parts are rinsed with de-ionized water in an ultrasonic bath for 15 minutes at Room temperature; followed by neutralization by immersing the parts in sodium bicarbonate solution at room temperature for 13 minutes. After the neutralization process, the parts are then rinsed in de-ionized water in an ultrasonic bath at room temperature for 15 minutes. The parts are then rinsed with isopropyl alcohol and finally dried in air at room temperature for few hours. Passivation treatments provide a controlled and uniformly oxidized surface state. The passivation leads to a dense and stable oxide film and improves corrosion resistance (decreases ion release). It has however practically no influence on the overall surface topography of titanium surface. The resulting layer of this chemical treatment is a TiO2 film in a thickness of two to six nanometers.

The main difference between the "nano-modification process" of the present invention and the current passivation processes is the heating process involved in the nano-modification process after the acidic treatment. In the typical passivation process the nitric acid treatment changes the oxygen content of the surface, but returns to normal after drying. In the process of the present invention the acid treatment is followed by a heat treatment at an elevated temperature (greater than 100° C.) which creates the desirable nanofeatures on the implant surface that decrease bacterial response.

Therefore, these implants contain antimicrobial properties which reduce microbial-related infections.

BRIEF SUMMARY OF THE INVENTION

Described herein are methods of manufacturing nano-modified implants that contain antimicrobial properties. The methods may include: a) immersing the implant in acid at a concentration of 0.5N to 15N for 5 minutes to 120 minutes; b) rinsing the acid-treated implant in an aqueous cleaner having a pH of 6 to 8 to remove the acid; and c) heating the rinsed implant at a temperature between 100° Celsius and 800° Celsius for a minimum of 30 minutes.

The implants that result from these methods contain a nano-modified surface that is resistant to microbial cell adhesion and ultimately reduce biomaterials-related infections at the implant site. The nano-modified implants described herein may contain a surface roughness of 20 nanometers to 80 nanometers; a surface with at least one surface feature wherein the width or height of the at least one surface feature is 1 nanometer or greater; and/or a surface energy as measured in contact angles of 10 degrees to 60 degrees.

These nano-modified implants can be used for decreasing microbial response at the site of implant when prepared by the methods described herein.

BRIEF DESCRIPTION OF THE DRAWINGS

The figures are graphical illustrations of the growth of *Staphyloccocus epidermidis* or *Staphyloccocus aureus* on nano-modified implants prepared by the methods described herein:

FIGS. 13 through 19 and 34 through 40 are atomic force microscopy (AFM) scans of the surface of nano-modified implants prepared by the methods described herein. The AFM images support that after nitric acid treatment, surface roughness of the titanium based implants increased with the greatest number of nanoscale surface features observed for the greatest nitric acid concentration, treatment time, and heating temperature. This is supported by both the AFM images and the adjacent line scans which represent a plot of the x distance with corresponding height changes; and FIGS. 20 through 27 and 41 through 56 are graphical illustrations of the correlation between material characterization and bacterial adhesion of nano-modified implants prepared by the methods described herein. These plots demonstrate that the feature width has a greater impact on the antimicrobial properties than the feature height. The plots further show the ability to decrease bacteria growth by increasing nanoscale surface feature width on either porous or non-porous titanium samples, which can be accomplished by increasing nitric acid treatment concentration, increasing nitric acid treatment time, and increasing heating temperature.

DETAILED DESCRIPTION

Methods of Manufacturing Implants

Figure 1:
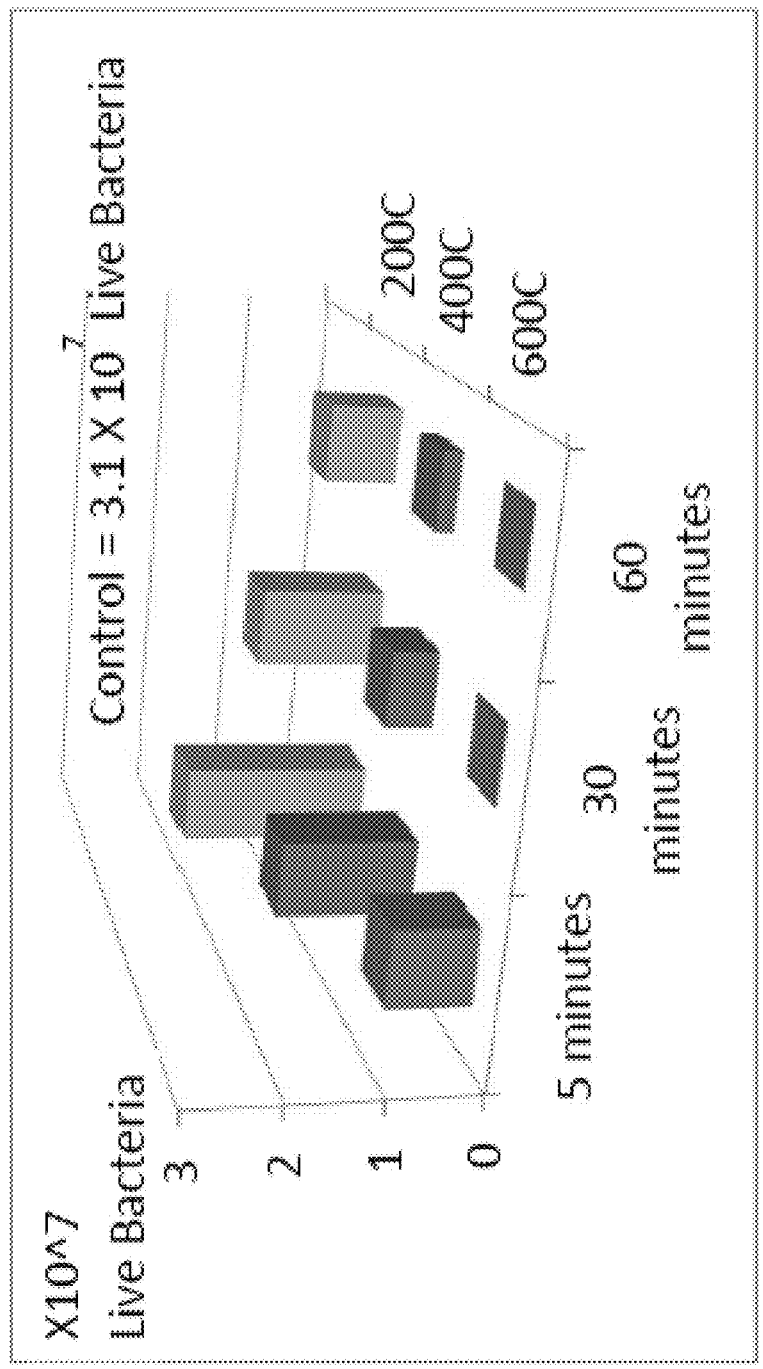
FIG. 1 shows the growth of *Staphyloccocus epidermidis* on non-porous titanium implants treated with 10N nitric acid at different times of treatment (5, 30, and 60 minutes) and then heat treated under different temperatures (200, 400, and 600° C.)

One aspect of the invention includes methods of manufacturing a metal implant which has a nano-modified surface that decreases microbial response, i.e., microbial adhesion to the implant. The methods of manufacturing the nano-modified implants comprise immersing an implant in an acid, rinsing the acid-treated implant, and heating the rinsed implant to create a nano-modified structure on the surface of the implant.

There is no limit to the type of material used for the implant. In one embodiment, the implant is made from titanium, for example, from commercially pure titanium, or a titanium alloy. Exemplary embodiments of the type of material used for the implant may also include cobalt, chromium, and stainless steel. The implant can also be made of porous or non-porous materials. In one embodiment, at least a portion of the metal is porous prior to immersing the implant in the acid.

The first step for modifying the surface of the implant involves immersing or soaking the implant in an acid solution to treat the implant. Without being bound by a particularly theory, it is believed that the acid treatment step alters the surface nanoscale topography through ion subtraction and ion deposition. The surface topography is concentration and temperature dependent. By increasing acid concentration and increasing temperature after the parts have been removed from the acid and rinsed, a more aggressive environment is provided for the acid to alter roughness.

The conditions for immersing or soaking the implant in the acid are not limited so long as the concentration of the acid and the time of immersion are sufficient to create the specific nanoscale surface features to decrease bacterial growth. In one embodiment, the concentration of the acid is about 0.5N to about 15N when the implant is immersed in the acid. In another embodiment, the concentration of the acid is about 1N to about 10N when the implant is immersed in the acid.

The amount of time that the implant is immersed in the acid is not limited. In certain embodiments, the implant is immersed in the acid for about 5 minutes to about 120 minutes. In another embodiment, the implant is immersed in the acid for about 10 minutes to about 60 minutes.

The type of acid used to immerse the implant is not limited. In certain embodiments, the acid is nitric acid, phosphoric acid, or sulfuric acid.

After the implant is immersed in the acid, the implant is then rinsed to remove the acid from the implant and to stop the reaction leading to the generation of nanoscale surface features. In one embodiment, the implant is rinsed or immersed in an aqueous solution to remove the acid from the implant. In another embodiment, the aqueous solution has a pH of about 6 to about 8. In yet another embodiment, the implant is rinsed with de-ionized water to remove the acid from the implant.

There is no limit to the amount of time used to rinse or immerse the implant to remove the acid. In one embodiment, the implant is rinsed with the aqueous solution for about 2 minutes to about 10 minutes.

After rinsing the acid-treated implant, the implant can then optionally be dried overnight prior to heating the implant. In one embodiment, drying the rinsed implant overnight is performed at room temperature. The implant may be heated to an elevated temperature (greater than 100° C.) during the drying process.

After rinsing the acid-treated implant, and optionally drying overnight, the acid treated and rinsed implant is subjected to a heating step. Without being bound by a particularly theory, it is believed that the heating of the implant further stops the reaction by removing the acid to stabilize the nanoscale topography.

There is no limit to the length of time of the heating step so long as the correct nanoscale surface features are generated as described herein. In one embodiment, the rinsed implant is heated for a minimum of about 30 minutes; however times less than 30 minutes are contemplated.

In one embodiment, the rinsed implant is heated at a temperature of about 100° Celsius to about 800° Celsius. In another embodiment, the rinsed implant is heated at a temperature of about 400° Celsius to about 600° Celsius.

The rate of temperature increase during the heating step can also be controlled. For example, the temperature of the implant during heating can be increased from ambient temperature to a predetermined temperature at a rate of about 10° Celsius per minute. Controlling the rate of temperature increase allows for a uniform drying of the surface to retain the desirable nanoscale surface topography.

In another embodiment, the implant is heated to a predetermined temperature of between about 100° Celsius to about 800° C. and held at this predetermined temperature for about 30 minutes to about 60 minutes.

In one embodiment, a method of manufacturing a metal implant comprises: a) immersing the implant in an acid at a concentration of about 0.5N to about 15N for about 5 minutes to about 120 minutes; b) rinsing the acid-treated implant in an aqueous cleaner having a pH of about 6 to about 8 to remove the acid; and c) heating the rinsed implant at a temperature of between about 100° Celsius to about 800° Celsius for a minimum of about 30 minutes.

Implants

Another aspect of the invention relates to nano-modified implants prepared by any of the methods described herein. Applicants have discovered that when an implant is prepared by the methods described herein, microbial responses, i.e., microbial cell adhesion to the surface implant is significantly decreased compared to implants not prepared by the methods described herein (for example, implants prior to treatment with the acid). When the implant is prepared by the methods described herein, a nano-modified surface is created on at least a portion of the implant surface. Applicants have discovered that this nano-modified surface significantly reduces microbial cell adhesion to the implant. In addition, the surface chemistry of the implant is not altered when the implant is prepared the described methods. Therefore, the resulting nano-modified implants have less microbial adhesion yet retain its chemical properties Surface chemistry (or the percentage of elements at the surface and their bonding states, i.e., single, double, etc., can be determined using X-ray photoelectron spectroscopy.

The type of microorganism resistant to the nano-modified implant may include, for example, various types of bacteria. In one embodiment, the adhesion of bacterial cells to the nano-modified implant is less than 100% of the bacterial cell adhesion to an implant that was not prepared by the methods described herein, i.e., the implant prior to acid treatment. In another embodiment, the adhesion of bacterial cells to the nano-modified implant is less than 80%, 60%, 40%, 20%, 10%, or 5% of an implant that was not prepared by the methods described herein, i.e., the implant prior to acid treatment. In certain embodiments, the bacteria are *Staphylococcus epidermidis* or *Staphylococcus aureus*.

The nano-modified implants described herein may contain surface features with a measurable roughness. In one embodiment, the roughness of the nano-modified implant is at about 2 times to about 10 times the roughness of an implant that was not prepared by the methods described herein, i.e., the implant prior to acid treatment. In another embodiment, the roughness of the nano-modified implant is about 20 nanometers (nm) to about 80 nanometers (nm). In yet another embodiment, the roughness of the nano-modified implant is about 40 nanometers (nm) to about 80 nanometers (nm).

The nano-modified implants described herein may also contain surface features with a measurable width or height of a surface feature. For example, in one embodiment, the nano-modified implant has a surface feature with a width or height that is about 2 times to about 100 times the width or height of a surface feature of an implant that was not prepared by the methods described herein, i.e., the implant prior to acid treatment. In another embodiment, the nano-modified implant has a surface feature with a width or height of at about 1 nanometer (nm) or greater. In yet another embodiment, the nano-modified implant has a surface feature with a width or height of at about 5 nanometers (nm) to about 100 nanometers (nm). When the width and height of the surface features of the nano-modified implant are within these ranges, the implant surface is particularly resistant to microbial cell adhesion.

The nano-modified implants described herein have a surface energy (wettability), as measured in contact angles, less than the surface energy of implants that were not prepared by the methods described herein, i.e., the implant prior to acid treatment. In one embodiment, the surface energy of the nano-modified implant is less than 80%, 60%, 40%, 20%, 10%, or 5% of an implant that was not prepared by the methods described herein, i.e., the implant prior to acid treatment. In another embodiment, the nano-modified implant has a surface energy (wettability) as measured by contact angle of about 10 degrees to about 60 degrees.

Methods of Use

Another aspect of the invention relates to methods of using the nano-modified implants described herein for decreasing microbial response of the implant in a host mammal. In one embodiment, the method includes: 1) preparing a site for receipt of the nano-modified implant in a mammal; and 2) inserting the nano-modified implant into the site. When using the nano-modified implants described herein for such methods, microbial adhesion, for example, bacterial adhesion, to the implant and at the site of implant, is significantly reduced compared to those implants that have not been prepared by the methods described herein. Ultimately, this results in less proliferation of the microbial cells and a reduced chance of the formation of a biofilm at the site of implant.

EXAMPLES

Nano-modified implants were prepared according to the methods described herein. Commercially pure titanium implants, both porous and non-porous (flat), were obtained and immersed in either 1N, 5N, or 10N nitric acid ($HN_{O3}$) for either 5 minutes, 30 minutes, or 60 minutes. The implants were then cleaned with copious amounts of deionized water using a squirt bottle for approximately 5 minutes each. The washed implants were dried overnight before heating at either 200° C., 400° C., or 600° C. in air at a ramp rate of 10° C./minute). The nano-modified implants were then characterized for reduced bacterial adhesion, roughness, surface chemistry, and surface energy (wettability). As a control, titanium implants that were not subjected to the acid treatment, rinsing, or heating steps were also characterized for bacterial adhesion, roughness, surface chemistry, and surface energy (wettability).

Example 1

Bacterial Adhesion

Bacterial cell lines of biofilm-producing *Staphylococcus epidermidis* and *Staphylococcus aureus* were obtained in freeze dried form from the American Type Culture Collection (ATCC). The cells were propagated in Luria broth consisting of 10 g tryptone, 5 g yeast extract, and 5 g NaCl per liter of distilled water (all chemicals obtained from Sigma-Aldrich Company). Once the second passage of bacteria reached its stationary phase, the second passage was frozen in one part Luria bacteria broth and one part glycerol. All experiments were conducted from this frozen stock. One day prior to bacterial seeding onto the nano-modified implants, a sterile 10 mL loop was used to withdraw bacteria from the frozen stock and to inoculate a glass test tube with 3 mL of Luria broth. The test tube was agitated for approximately 16 h in an Innova 4000 incubator-shaker (New Brunswick Science) at 37° C. and 250 rpm.

Bacteria were then passed to a second 3 mL test tube of Luria broth and incubated under the same conditions for approximately 5 h (until the Luria broth was cloudy). Bacteria concentration was assessed via optical density reading. For this purpose, the Luria broth-bacteria mixture was placed in a polystyrene test tube (75×12 mm2; Starstedt) and color change determined in an appropriately calibrated VITEK colorimeter. If necessary, the sample was diluted with Luria broth to attain 30% transmittance. This transmittance equates with a three on the McFarland scale; resulting in an estimation of 900,000,000 cells/mL. Dilutions were completed until the estimated bacteria concentration was 10,000,000 cells/mL. The dilution media consisted of Dulbecco's modified eagle medium (DMEM; Gibco) supplemented with bovine fetal bovine serum (FBS; Hyclone), 2.16×10-3 g/mL beta-glycerophosphate (Sigma), and 5×10-5 g/mL ascorbate (Sigma).

Prior to seeding onto the nano-modified implants, implants of interest to the present study were placed into a 12-well culture dish (Fisher Scientific) and were washed twice with PBS. Bacteria were then seeded at 20,000,000 bacteria per well and were allowed to adhere to the implants for 1 hour in a standard bacteria culture incubator (at a 37° C., humidified, 5% CO2, and 20% O2 environment). At the end of the prescribed time period, the media was aspirated, and the substrates were washed twice with TBS (Sigma). The bacteria remaining on the implants after washing were stained using a live/dead assay (Molecular Probes) at room temperature. Bacterial live and dead cell counts were then completed in situ using a laser confocal microscope at 600×resulting in a field of view of 200×200 mm. Ten fields of view were averaged for each substrate. Experiments were completed in triplicate and repeated three times The results of the bacterial adhesion study are summarized in Tables 1-4 below. Representative illustrations are demonstrated in FIGS. 1-4. The results indicate that when the implant is prepared by the methods described herein, the resulting nano-modified implant significantly inhibits bacterial adhesion to the implant compared to the control implant.

TABLE 1

Growth of *Staphyloccocus epidermidis* on Non-Porous Nano-Modified Titanium Implants

Figure 2:
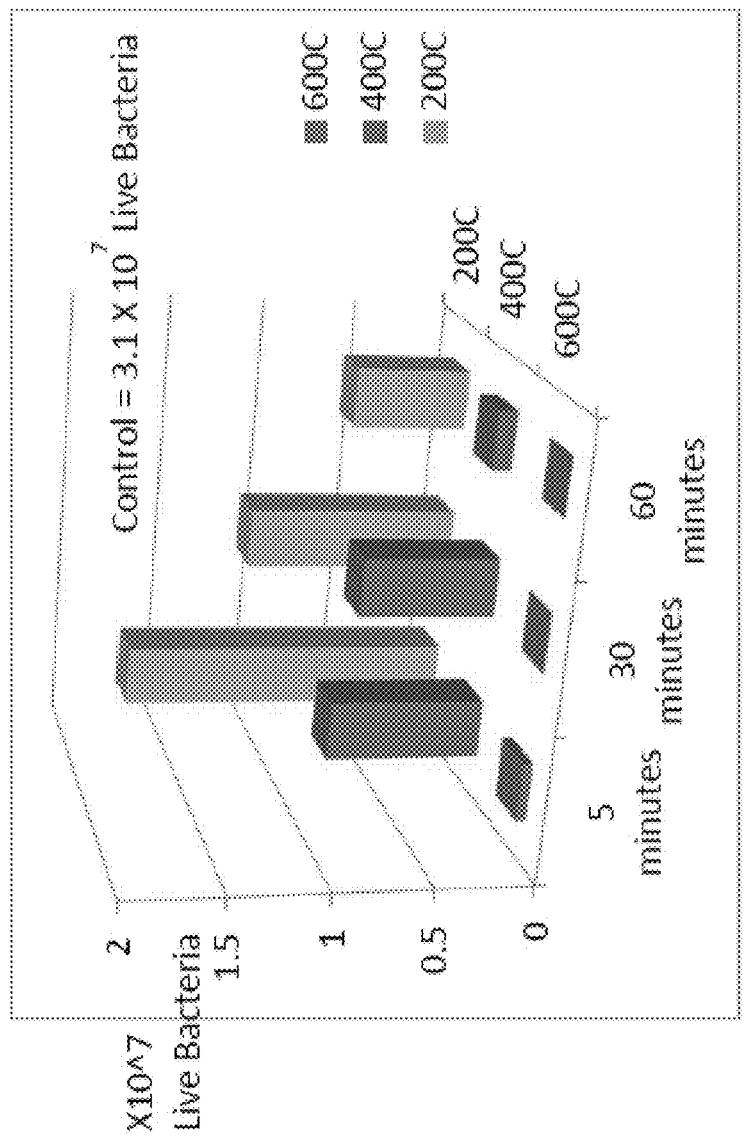
FIG. 2 shows the growth of *Staphyloccocus epidermidis* on porous titanium implants treated with 10N nitric acid at different times of treatment (5, 30, and 60 minutes) and then heat treated under different temperatures (200, 400, and 600° C.)'
Figure 3:
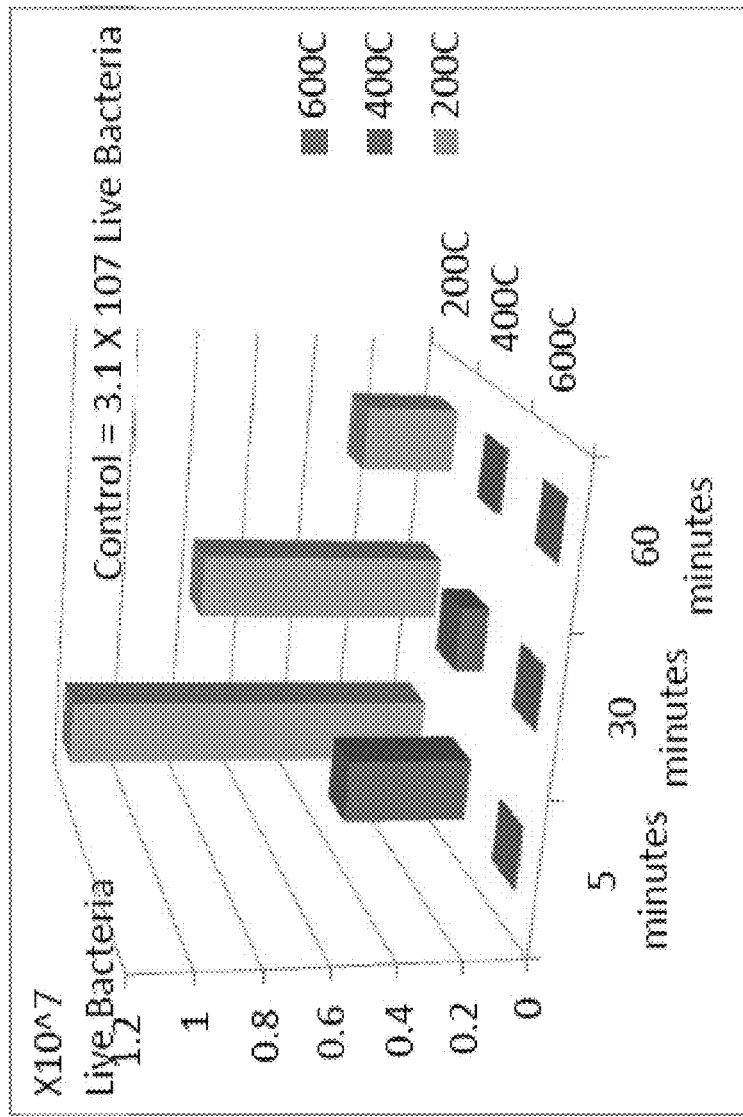
FIG. 3 shows the growth of *Staphyloccocus aureus* on non-porous titanium implants treated with 10N nitric acid at different times of treatment (5, 30, and 60 minutes) and then heat treated under different temperatures (200, 400, and 600° C.)

| Concentration of Acid | Time in Acid | Temp of Heating | Cells (×10$^7$) | % Control | FIG. |
|---|---|---|---|---|---|
| Control | — | — | 3.1 | 100% | FIG. 1-3 |
| 1N HNO$_3$ | 5 min | 200° C. | 2.1 | 68% | FIG. 1 |
| 1N HNO$_3$ | 30 min | 200° C. | 1.4 | 45% | FIG. 1 |
| 1N HNO$_3$ | 60 min | 200° C. | 0.8 | 26% | FIG. 1 |
| 1N HNO$_3$ | 5 min | 400° C. | 1.5 | 48% | FIG. 1 |
| 1N HNO$_3$ | 30 min | 400° C. | 0.5 | 16% | FIG. 1 |
| 1N HNO$_3$ | 60 min | 400° C. | 0.2 | 6% | FIG. 1 |
| 1N HNO$_3$ | 5 min | 600° C. | 0.9 | 30% | FIG. 1 |
| 1N HNO$_3$ | 30 min | 600° C. | 0.03 | 1% | FIG. 1 |
| 1N HNO$_3$ | 60 min | 600° C. | 0.007 | 0.2% | FIG. 1 |
| 5N HNO$_3$ | 5 min | 200° C. | 1.7 | 55% | FIG. 2 |
| 5N HNO$_3$ | 30 min | 200° C. | 1.1 | 35% | FIG. 2 |
| 5N HNO$_3$ | 60 min | 200° C. | 0.6 | 19% | FIG. 2 |
| 5N HNO$_3$ | 5 min | 400° C. | 0.8 | 26% | FIG. 2 |
| 5N HNO$_3$ | 30 min | 400° C. | 0.7 | 23% | FIG. 2 |
| 5N HNO$_3$ | 60 min | 400° C. | 0.1 | 3% | FIG. 2 |
| 5N HNO$_3$ | 5 min | 600° C. | 0.05 | 2% | FIG. 2 |
| 5N HNO$_3$ | 30 min | 600° C. | 0.01 | 0.3% | FIG. 2 |
| 5N HNO$_3$ | 60 min | 600° C. | 0.001 | 0.03% | FIG. 2 |
| 10N HNO$_3$ | 5 min | 200° C. | 1.2 | 39% | FIG. 3 |
| 10N HNO$_3$ | 30 min | 200° C. | 0.8 | 26% | FIG. 3 |
| 10N HNO$_3$ | 60 min | 200° C. | 0.3 | 10% | FIG. 3 |
| 10N HNO$_3$ | 5 min | 400° C. | 0.4 | 13% | FIG. 3 |
| 10N HNO$_3$ | 30 min | 400° C. | 0.09 | 3% | FIG. 3 |
| 10N HNO$_3$ | 60 min | 400° C. | 0.01 | 0.3% | FIG. 3 |
| 10N HNO$_3$ | 5 min | 600° C. | 0.01 | 0.3% | FIG. 3 |
| 10N HNO$_3$ | 30 min | 600° C. | 0.006 | 0.2% | FIG. 3 |
| 10N HNO$_3$ | 60 min | 600° C. | 0.0001 | 0.003% | FIG. 3 |

TABLE 2

Growth of *Staphyloccocus epidermidis* on Porous Nano-Modified Titanium Implants

Figure 4:
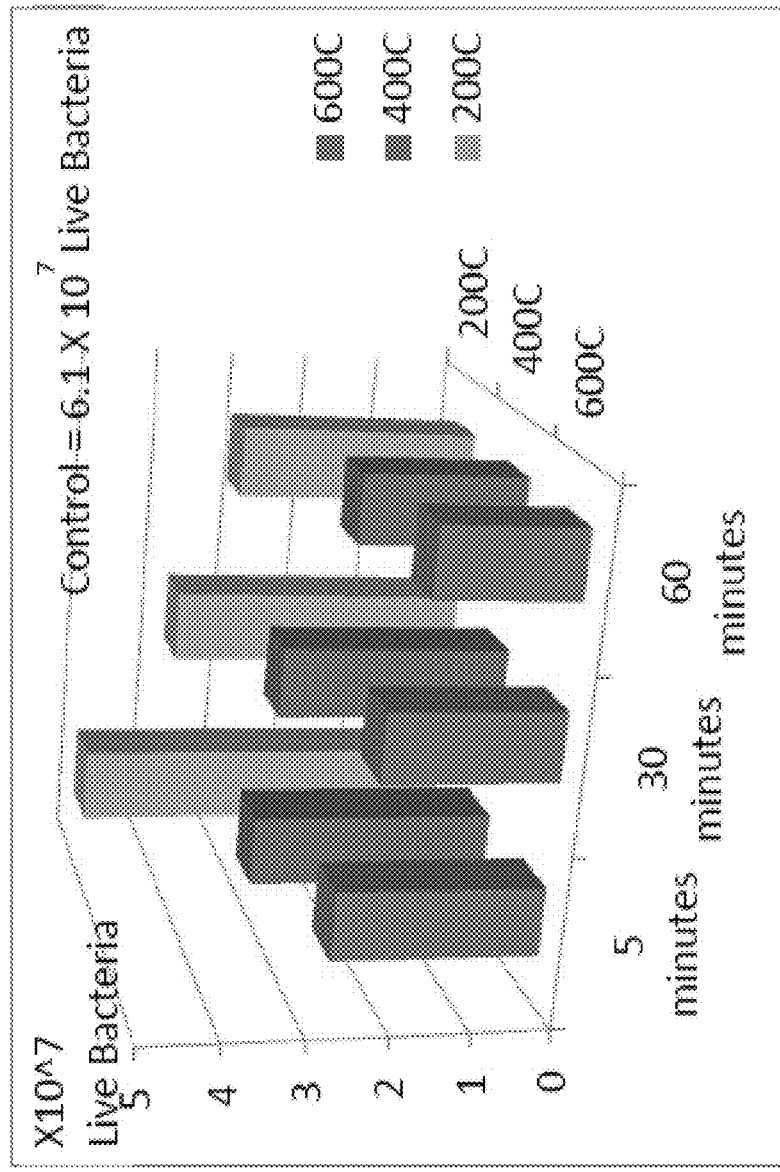
FIG. 4 shows the growth of *Staphyloccocus aureus* on porous titanium implants treated with 10N nitric acid at different times of treatment (5, 30, and 60 minutes) and then heat treated under different temperatures (200, 400, and 600° C.). For each graph, results show that treating in 10N Nitric Acid for longer periods of time followed by heating at higher temperatures maximizes bacterial inhibition. Controls represent untreated respective samples.
Figure 5:
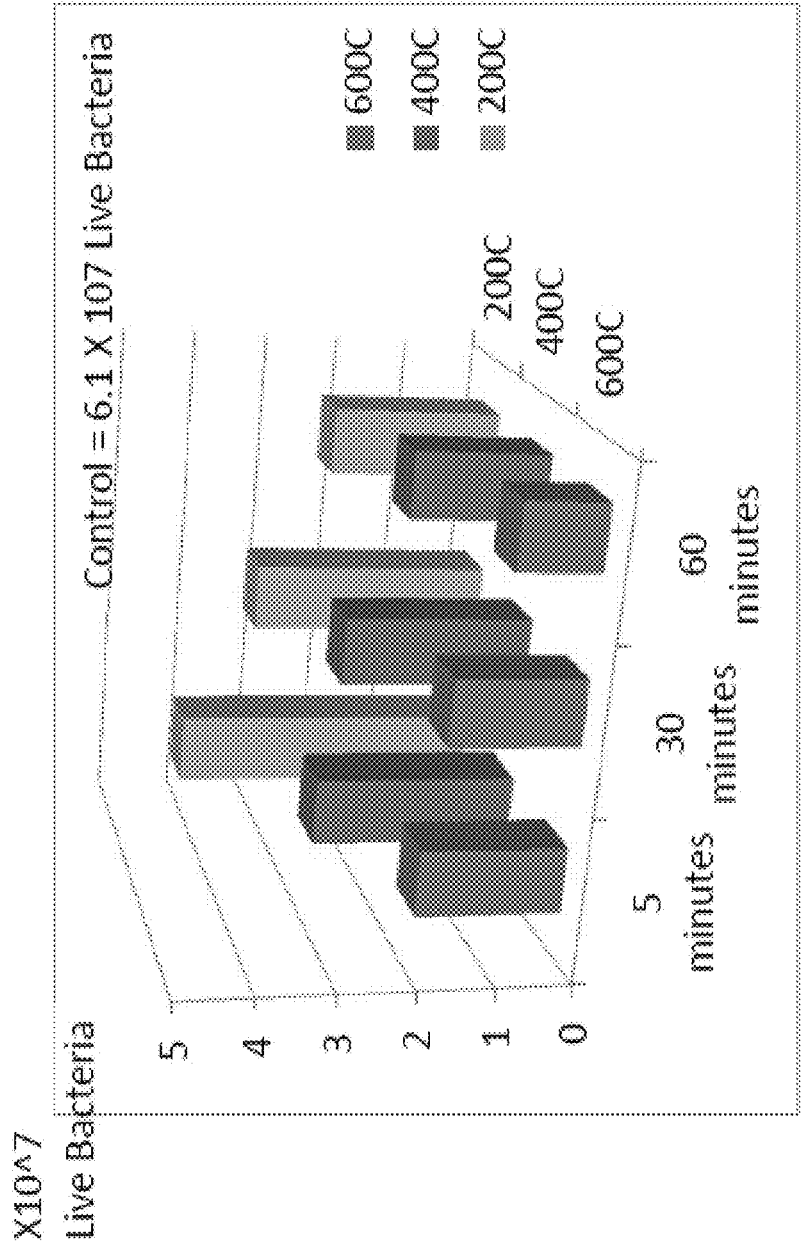
FIGS. 5 through 12 and 28 through 33 are scanning electron microscopy images (SEM) of nano-modified implants prepared by the methods described herein. The SEM images demonstrate etching of the titanium based surface with nitric acid increase surface roughness with the greatest number of nanoscale surface features observed for the greatest nitric acid concentrations, treatment time, and heating temperature'
Figure 6:
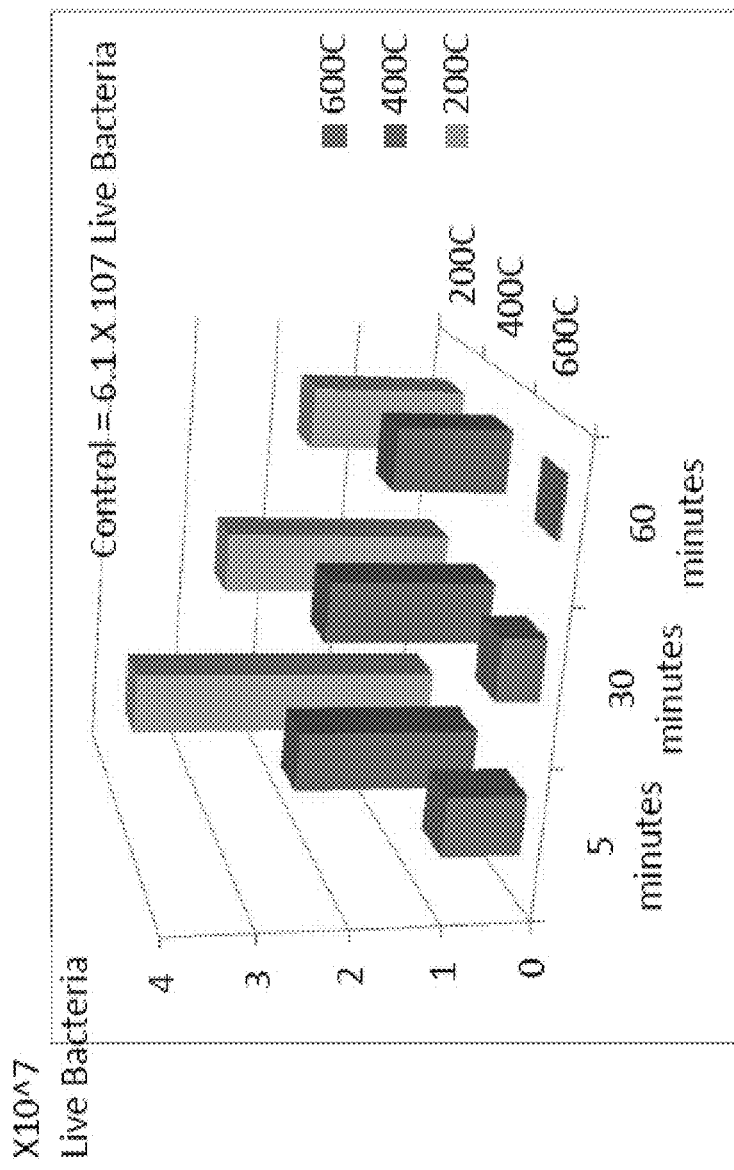

| Concentration of Acid | Time in Acid | Temp of Heating | Cells (×10$^7$) | % Control | FIG. |
|---|---|---|---|---|---|
| Control | — | — | 6.1 | 100% | FIG. 4-6 |
| 1N HNO$_3$ | 5 min | 200° C. | 4.9 | 80% | FIG. 4 |
| 1N HNO$_3$ | 30 min | 200° C. | 3.8 | 62% | FIG. 4 |
| 1N HNO$_3$ | 60 min | 200° C. | 3.1 | 51% | FIG. 4 |
| 1N HNO$_3$ | 5 min | 400° C. | 3.1 | 51% | FIG. 4 |
| 1N HNO$_3$ | 30 min | 400° C. | 2.9 | 48% | FIG. 4 |
| 1N HNO$_3$ | 60 min | 400° C. | 2.1 | 34% | FIG. 4 |
| 1N HNO$_3$ | 5 min | 600° C. | 2.6 | 43% | FIG. 4 |
| 1N HNO$_3$ | 30 min | 600° C. | 2.2 | 36% | FIG. 4 |
| 1N HNO$_3$ | 60 min | 600° C. | 1.8 | 30% | FIG. 4 |
| 5N HNO$_3$ | 5 min | 200° C. | 4.1 | 67% | FIG. 5 |
| 5N HNO$_3$ | 30 min | 200° C. | 3.2 | 52% | FIG. 5 |
| 5N HNO$_3$ | 60 min | 200° C. | 2.3 | 38% | FIG. 5 |
| 5N HNO$_3$ | 5 min | 400° C. | 2.7 | 44% | FIG. 5 |
| 5N HNO$_3$ | 30 min | 400° C. | 2.5 | 41% | FIG. 5 |
| 5N HNO$_3$ | 60 min | 400° C. | 1.8 | 30% | FIG. 5 |
| 5N HNO$_3$ | 5 min | 600° C. | 1.9 | 31% | FIG. 5 |
| 5N HNO$_3$ | 30 min | 600° C. | 1.7 | 28% | FIG. 5 |
| 5N HNO$_3$ | 60 min | 600° C. | 1.1 | 18% | FIG. 5 |
| 10N HNO$_3$ | 5 min | 200° C. | 3.7 | 61% | FIG. 6 |
| 10N HNO$_3$ | 30 min | 200° C. | 2.7 | 44% | FIG. 6 |
| 10N HNO$_3$ | 60 min | 200° C. | 1.8 | 30% | FIG. 6 |
| 10N HNO$_3$ | 5 min | 400° C. | 2.1 | 34% | FIG. 6 |
| 10N HNO$_3$ | 30 min | 400° C. | 1.9 | 31% | FIG. 6 |
| 10N HNO$_3$ | 60 min | 400° C. | 1.3 | 21% | FIG. 6 |
| 10N HNO$_3$ | 5 min | 600° C. | 0.9 | 15% | FIG. 6 |
| 10N HNO$_3$ | 30 min | 600° C. | 0.5 | 8% | FIG. 6 |
| 10N HNO$_3$ | 60 min | 600° C. | 0.04 | 0.7% | FIG. 6 |

TABLE 3

Growth of *Staphyloccocus aureus* on Non-Porous Nano-Modified Titanium Implants

Figure 7:
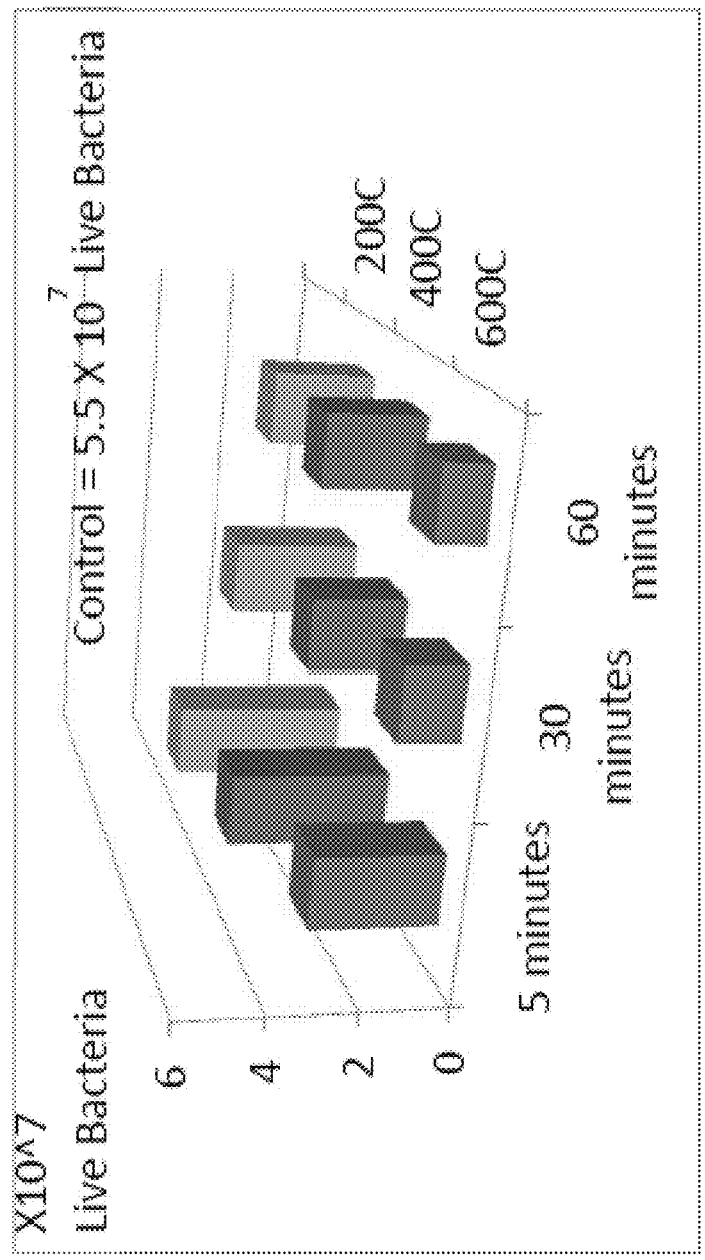
Figure 8:
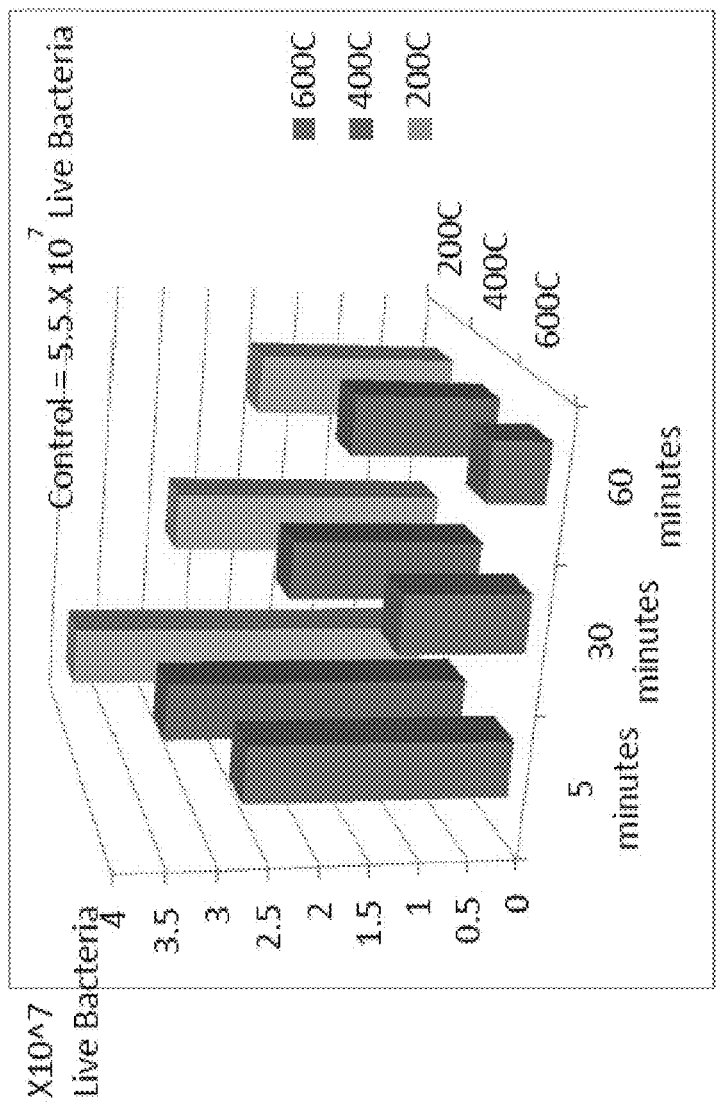
Figure 9:
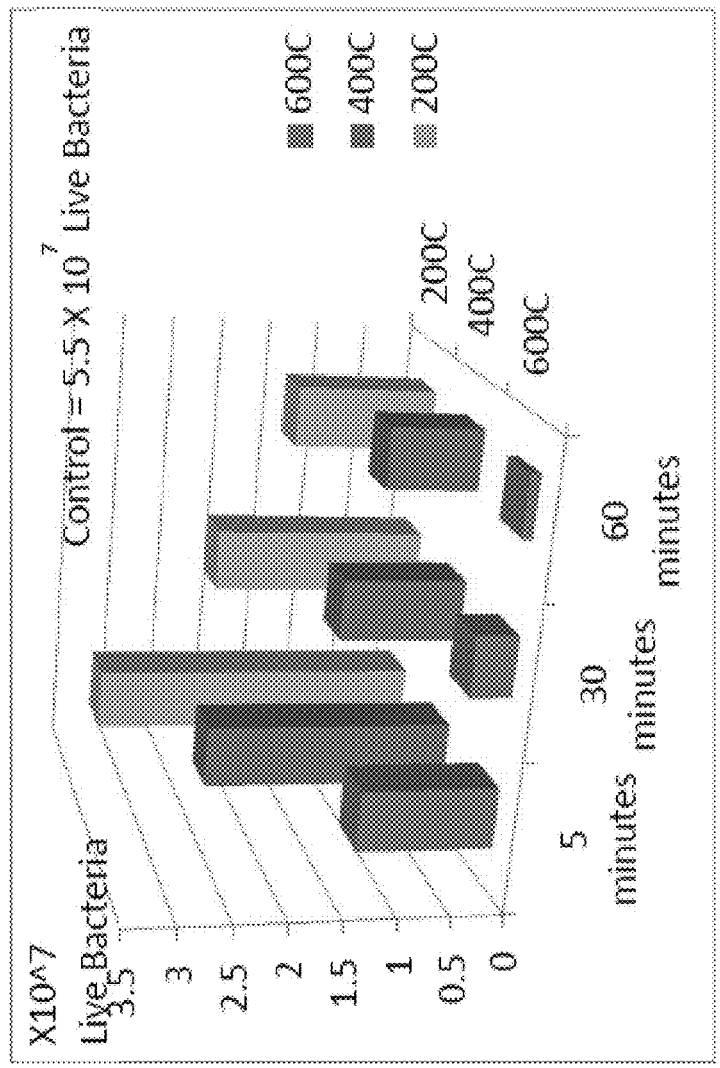

| Concentration of Acid | Time in Acid | Temp of Heating | Cells (×10$^7$) | % Control | FIG. |
|---|---|---|---|---|---|
| Control | — | — | 5.5 | 100% | FIG. 7-9 |
| 1N HNO$_3$ | 5 min | 200° C. | 4.1 | 75% | FIG. 7 |
| 1N HNO$_3$ | 30 min | 200° C. | 3.0 | 55% | FIG. 7 |
| 1N HNO$_3$ | 60 min | 200° C. | 2.4 | 44% | FIG. 7 |
| 1N HNO$_3$ | 5 min | 400° C. | 3.7 | 67% | FIG. 7 |
| 1N HNO$_3$ | 30 min | 400° C. | 2.2 | 40% | FIG. 7 |
| 1N HNO$_3$ | 60 min | 400° C. | 2.3 | 42% | FIG. 7 |
| 1N HNO$_3$ | 5 min | 600° C. | 2.9 | 53% | FIG. 7 |
| 1N HNO$_3$ | 30 min | 600° C. | 1.4 | 25% | FIG. 7 |
| 1N HNO$_3$ | 60 min | 600° C. | 1.1 | 20% | FIG. 7 |
| 5N HNO$_3$ | 5 min | 200° C. | 3.9 | 71% | FIG. 8 |
| 5N HNO$_3$ | 30 min | 200° C. | 2.9 | 53% | FIG. 8 |
| 5N HNO$_3$ | 60 min | 200° C. | 2.1 | 38% | FIG. 8 |
| 5N HNO$_3$ | 5 min | 400° C. | 3.2 | 58% | FIG. 8 |
| 5N HNO$_3$ | 30 min | 400° C. | 2.0 | 36% | FIG. 8 |
| 5N HNO$_3$ | 60 min | 400° C. | 1.5 | 27% | FIG. 8 |
| 5N HNO$_3$ | 5 min | 600° C. | 2.7 | 49% | FIG. 8 |
| 5N HNO$_3$ | 30 min | 600° C. | 1.3 | 24% | FIG. 8 |
| 5N HNO$_3$ | 60 min | 600° C. | 0.6 | 11% | FIG. 8 |
| 10N HNO$_3$ | 5 min | 200° C. | 3.2 | 58% | FIG. 9 |
| 10N HNO$_3$ | 30 min | 200° C. | 2.1 | 38% | FIG. 9 |
| 10N HNO$_3$ | 60 min | 200° C. | 1.4 | 25% | FIG. 9 |
| 10N HNO$_3$ | 5 min | 400° C. | 2.4 | 44% | FIG. 9 |
| 10N HNO$_3$ | 30 min | 400° C. | 1.2 | 22% | FIG. 9 |
| 10N HNO$_3$ | 60 min | 400° C. | 0.9 | 16% | FIG. 9 |
| 10N HNO$_3$ | 5 min | 600° C. | 1.3 | 24% | FIG. 9 |
| 10N HNO$_3$ | 30 min | 600° C. | 0.4 | 7% | FIG. 9 |
| 10N HNO$_3$ | 60 min | 600° C. | 0.1 | 2% | FIG. 9 |

TABLE 4

Growth of *Staphyloccocus aureus* on Porous Nano-Modified Titanium Implants

Figure 10:
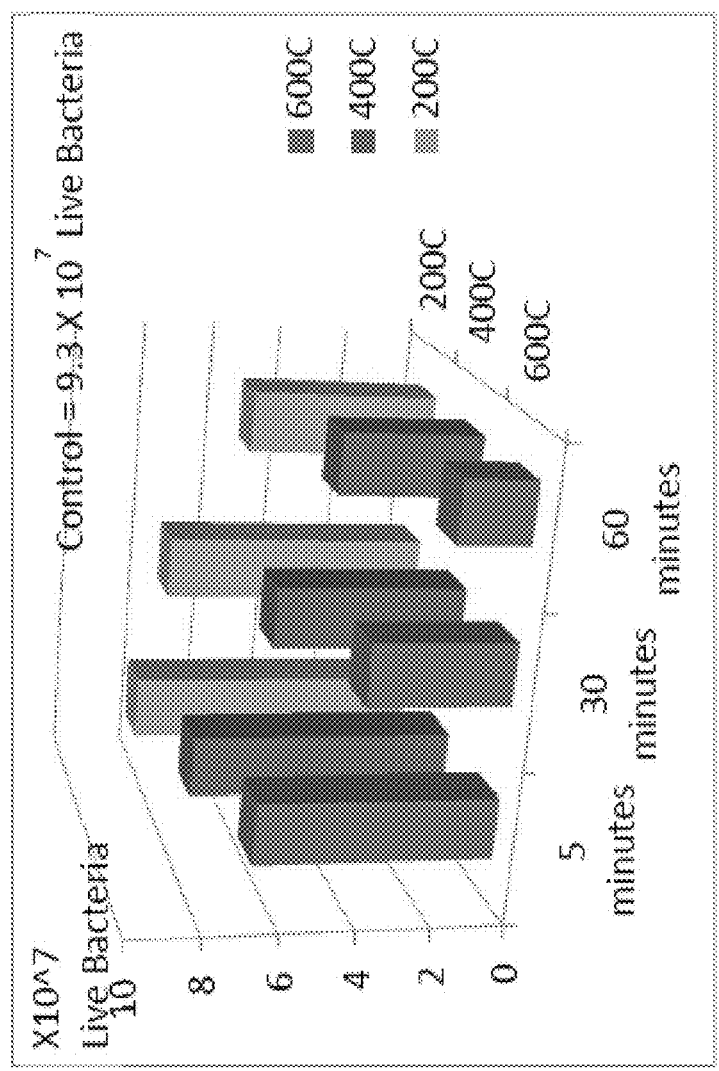
Figure 11:
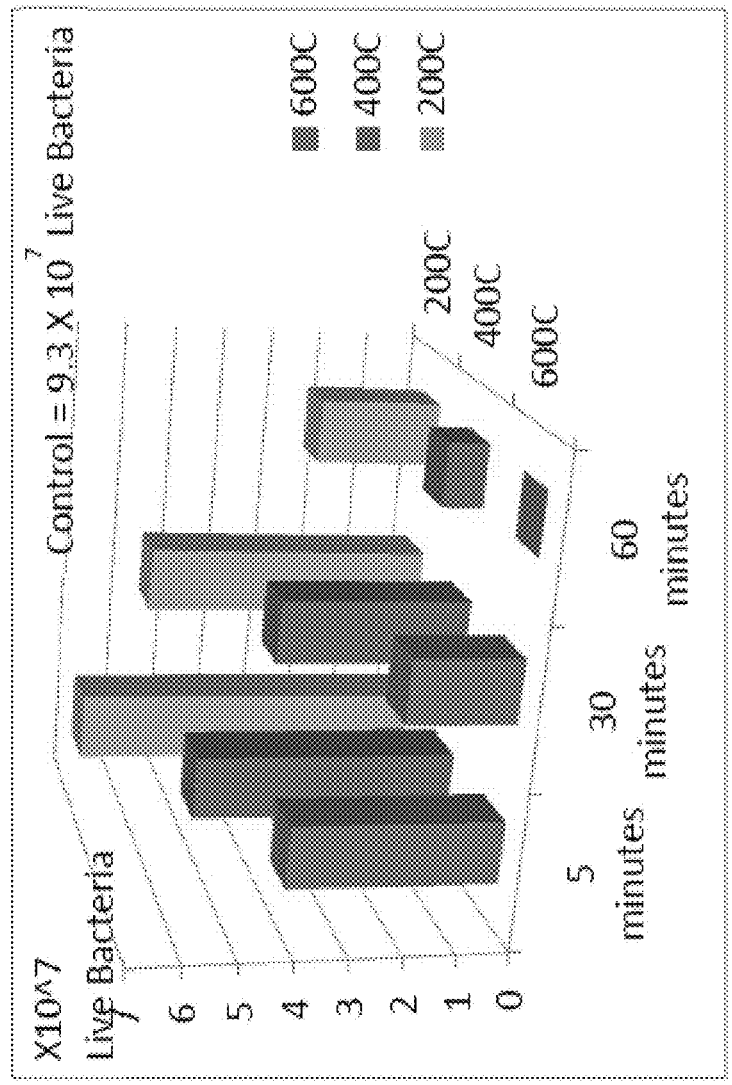
Figure 12:
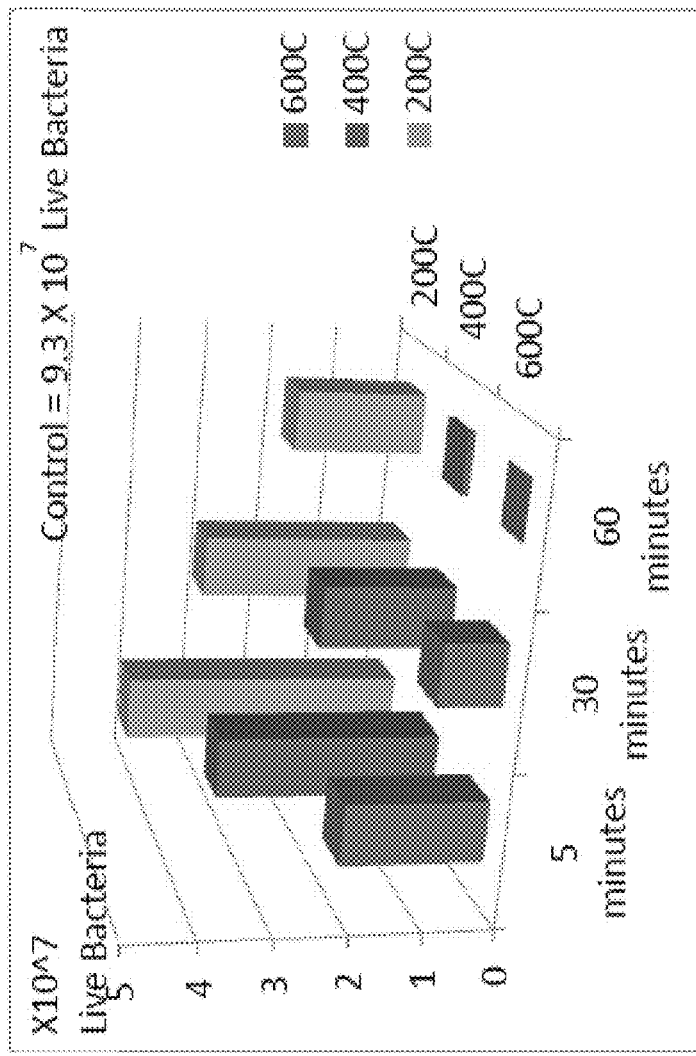
Figure 13:
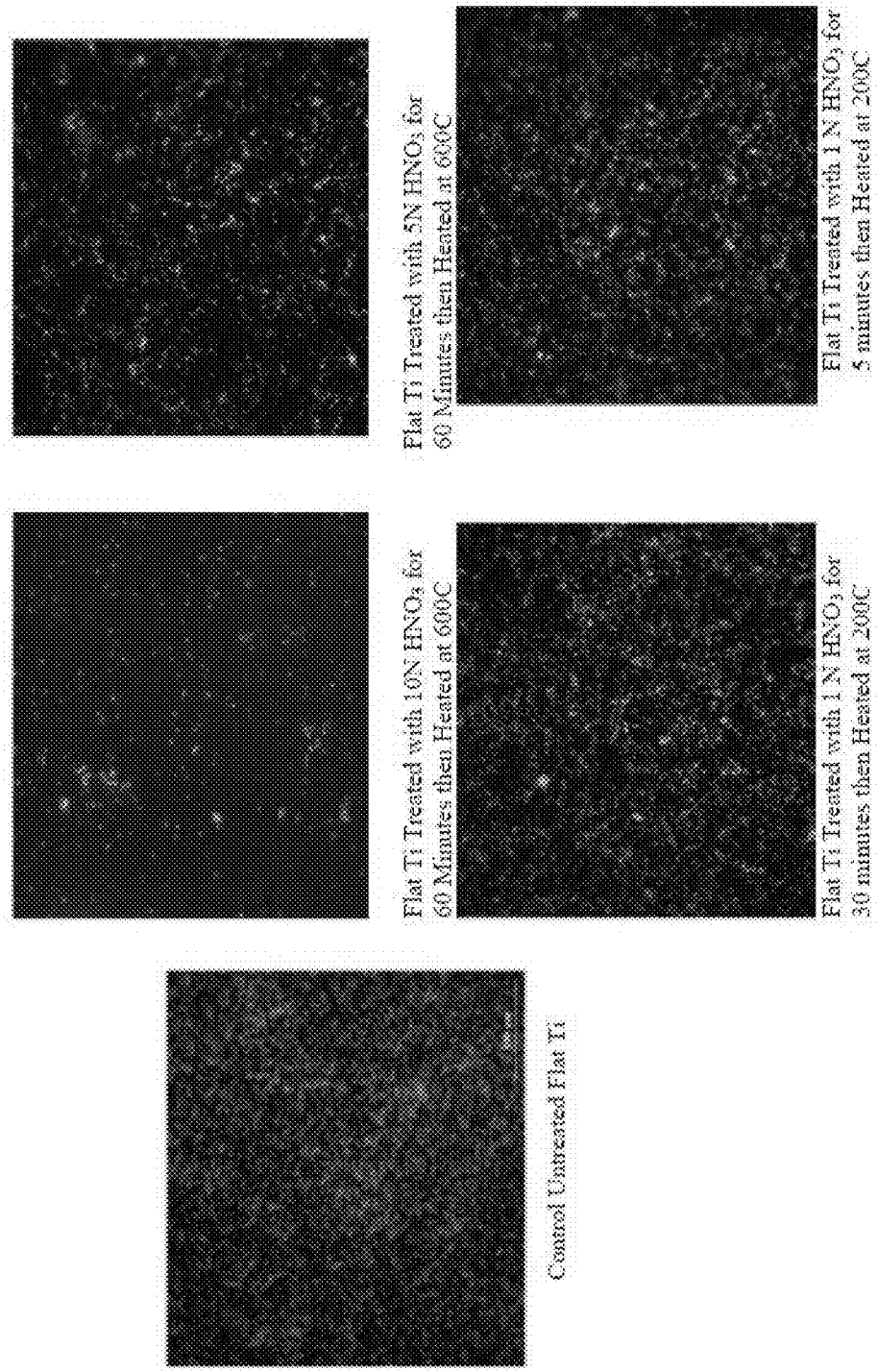
Figure 14:
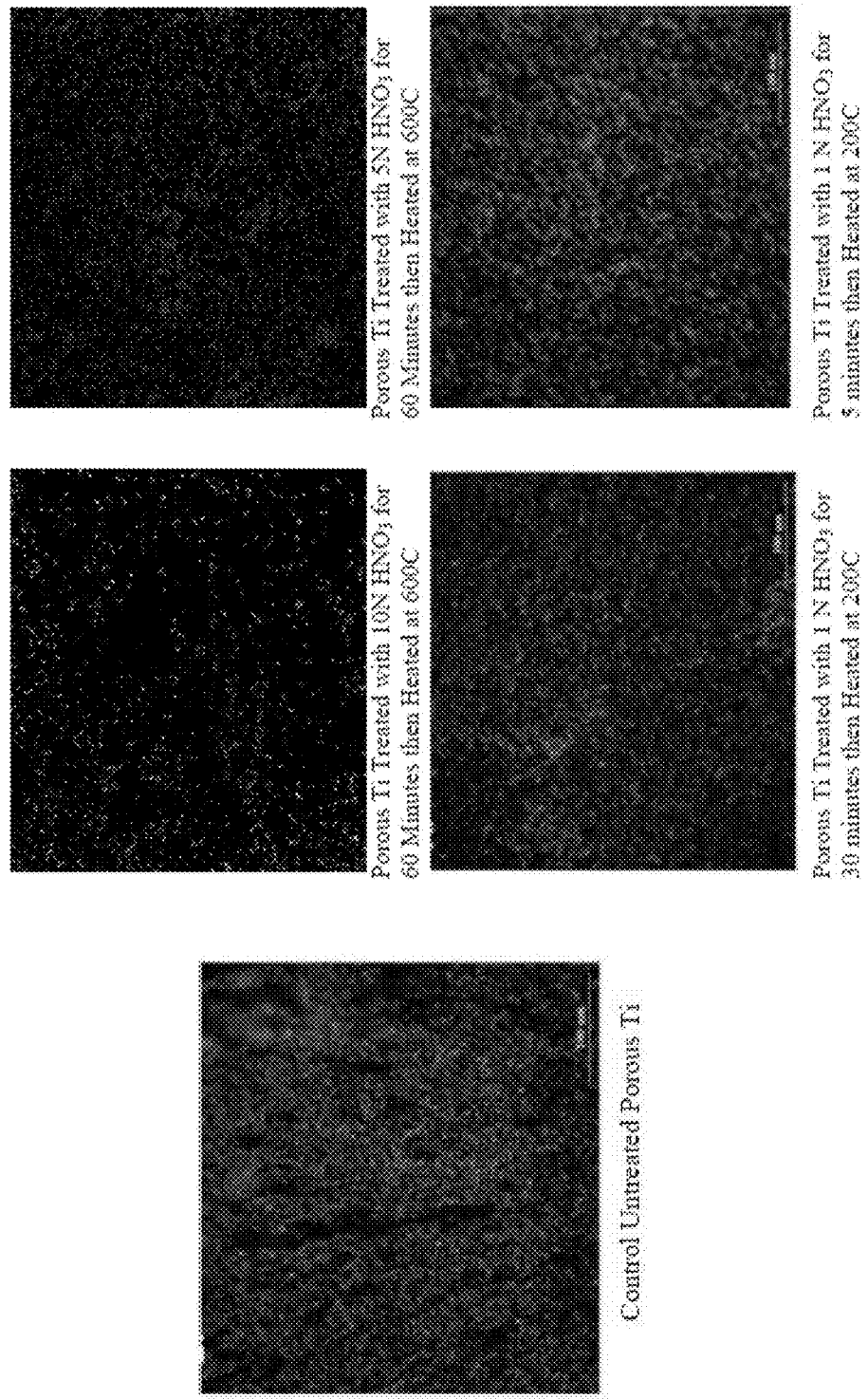
Figure 15:
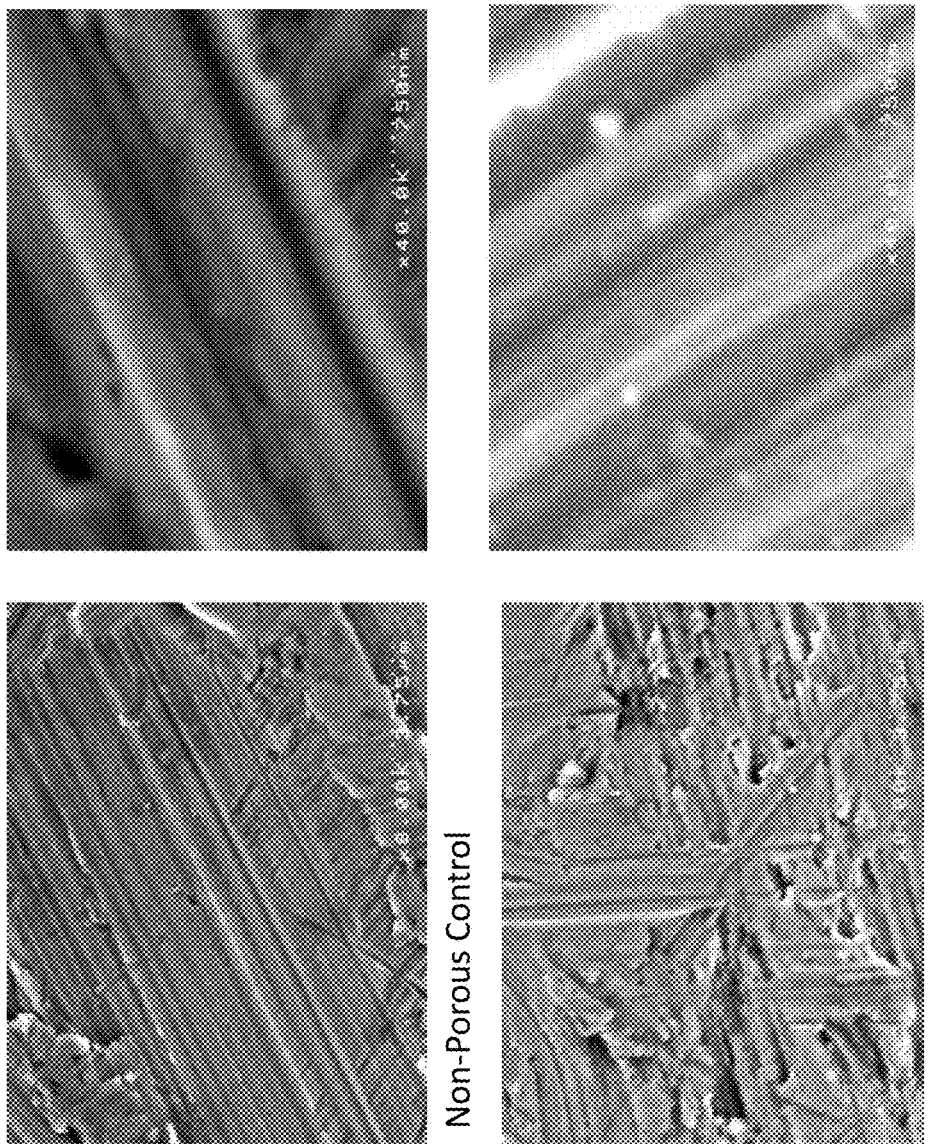
Figure 16:
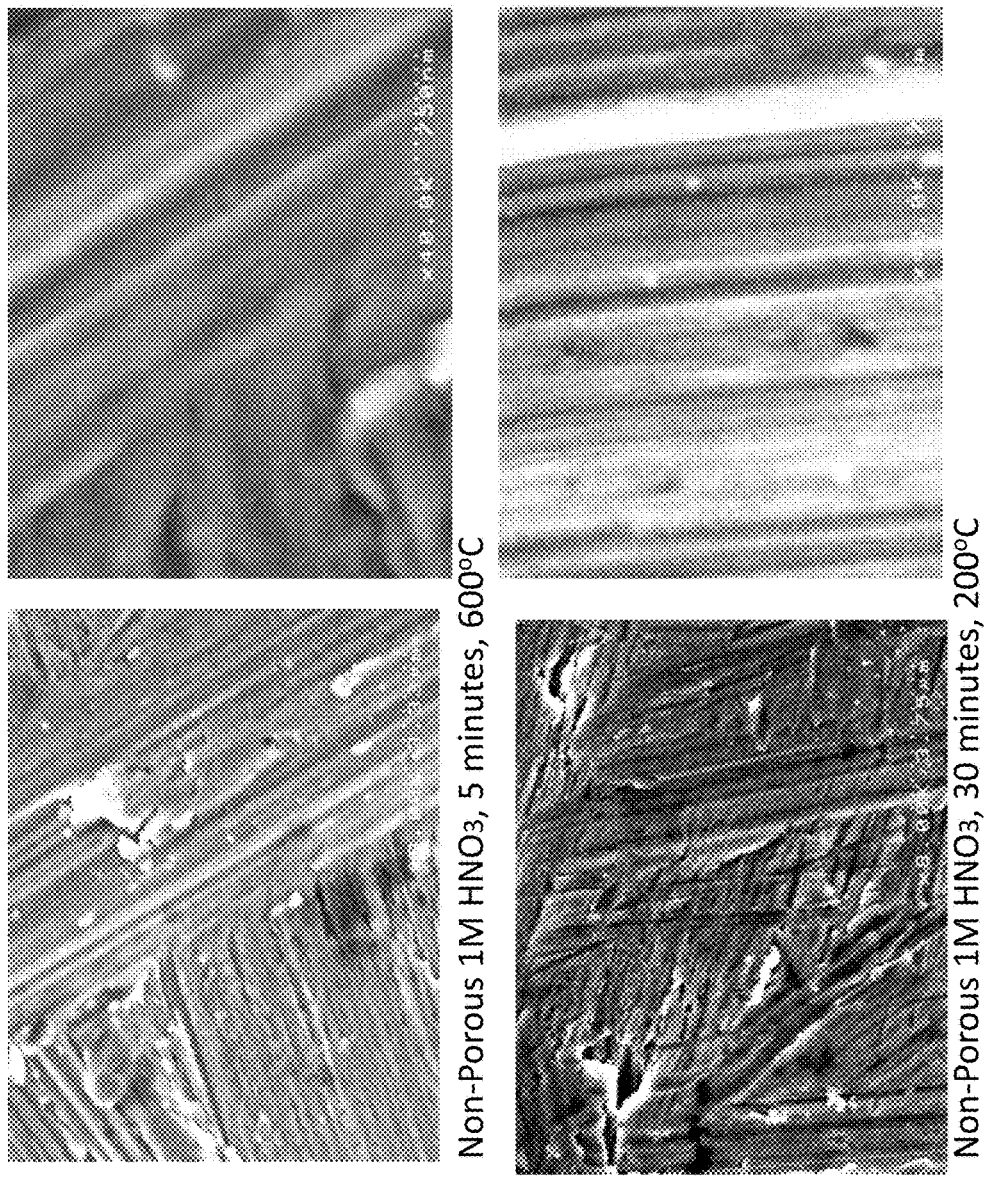
Figure 17:
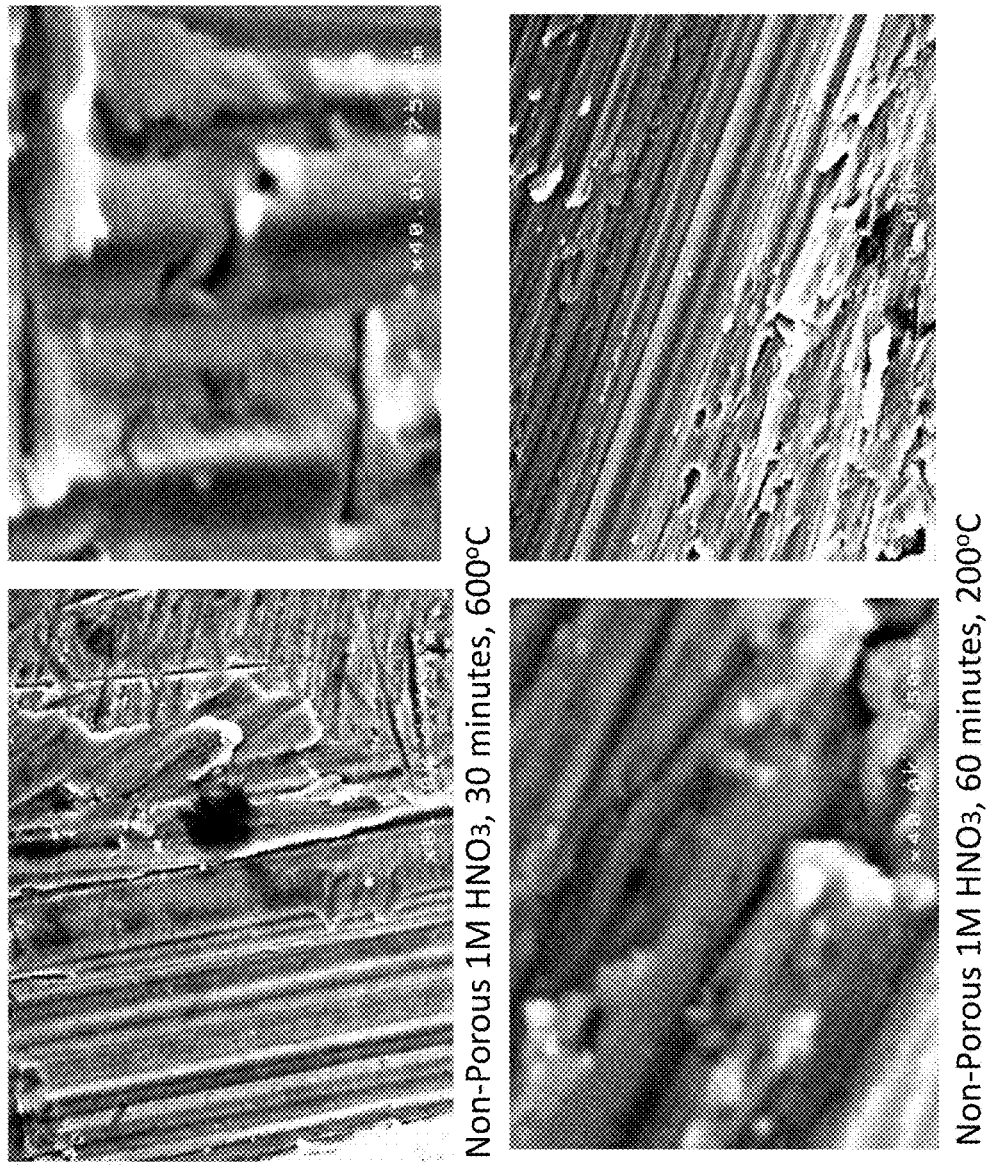
Figure 19:
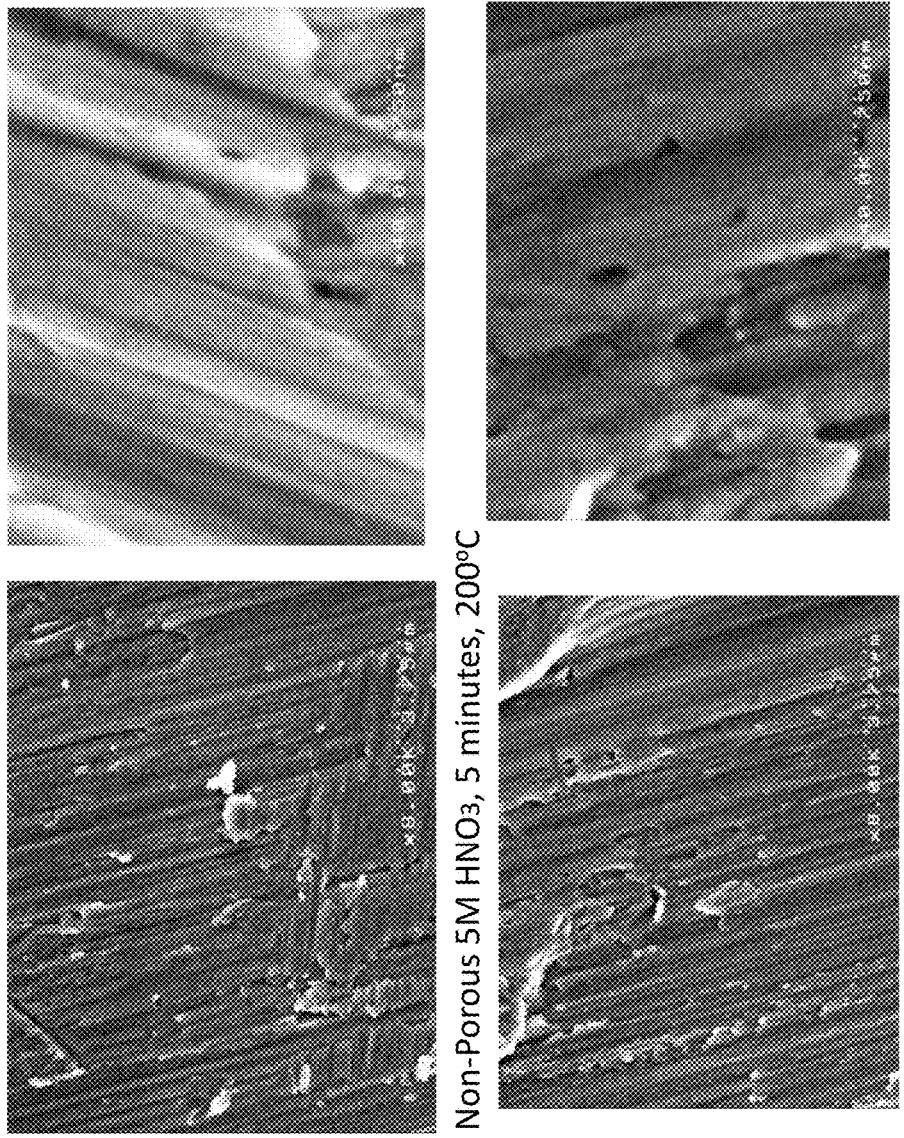
Figure 20:
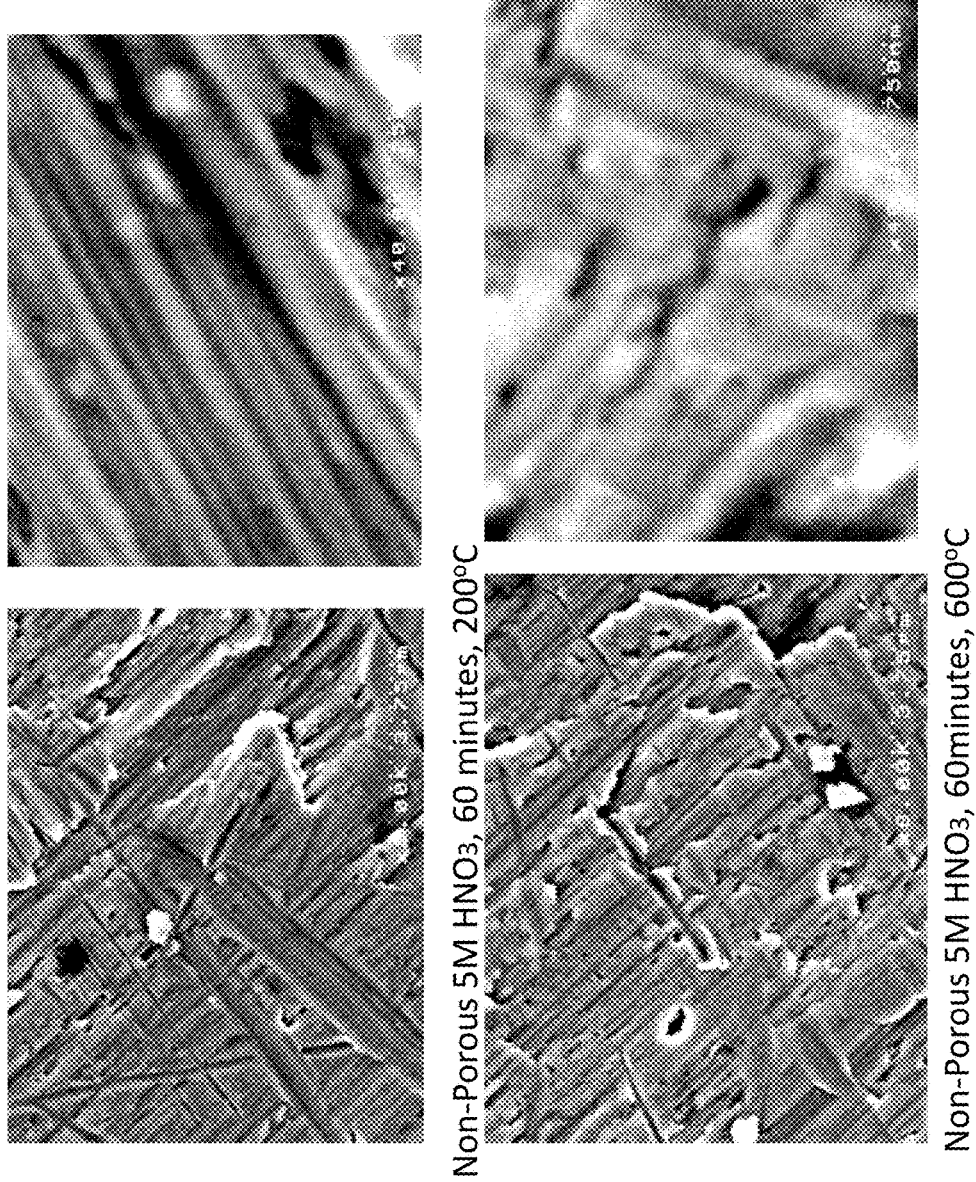
Figure 21:
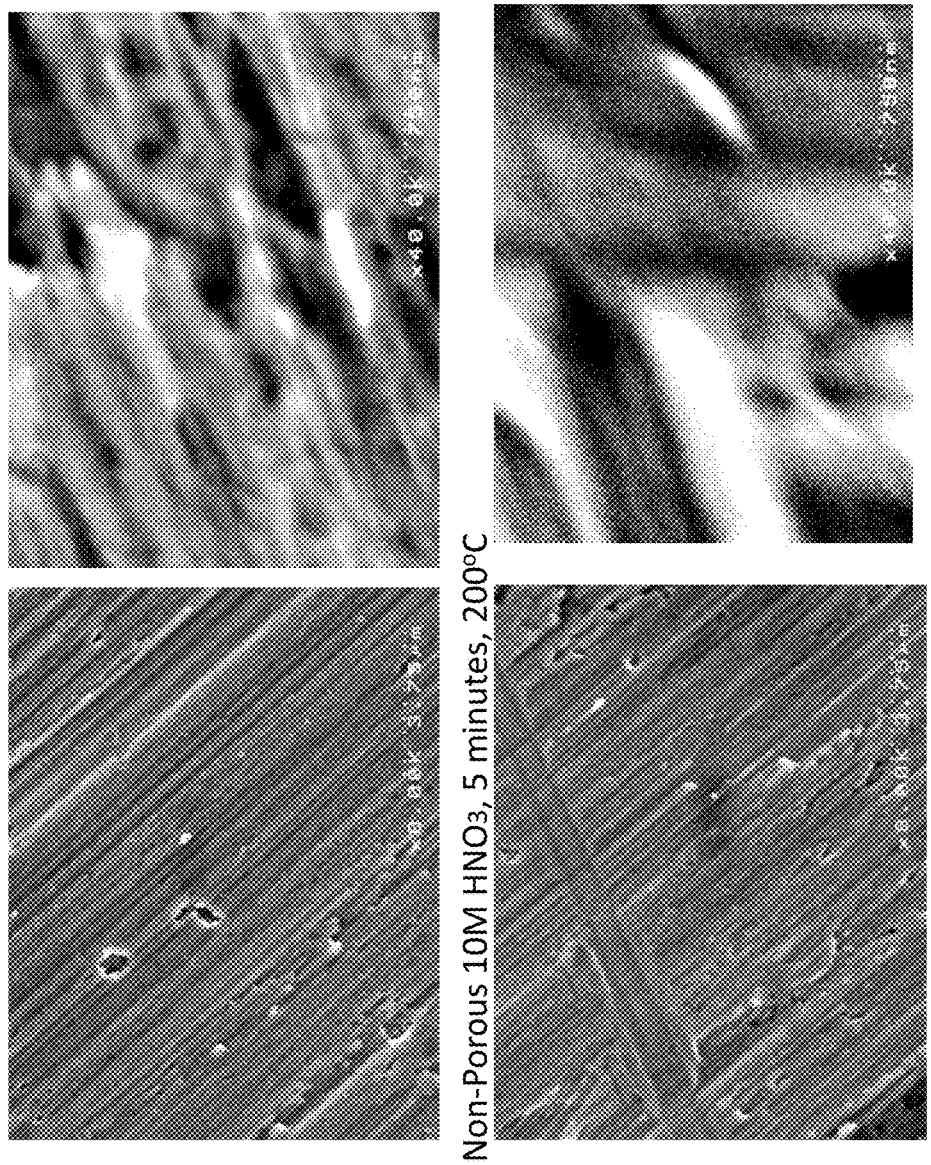
Figure 22:
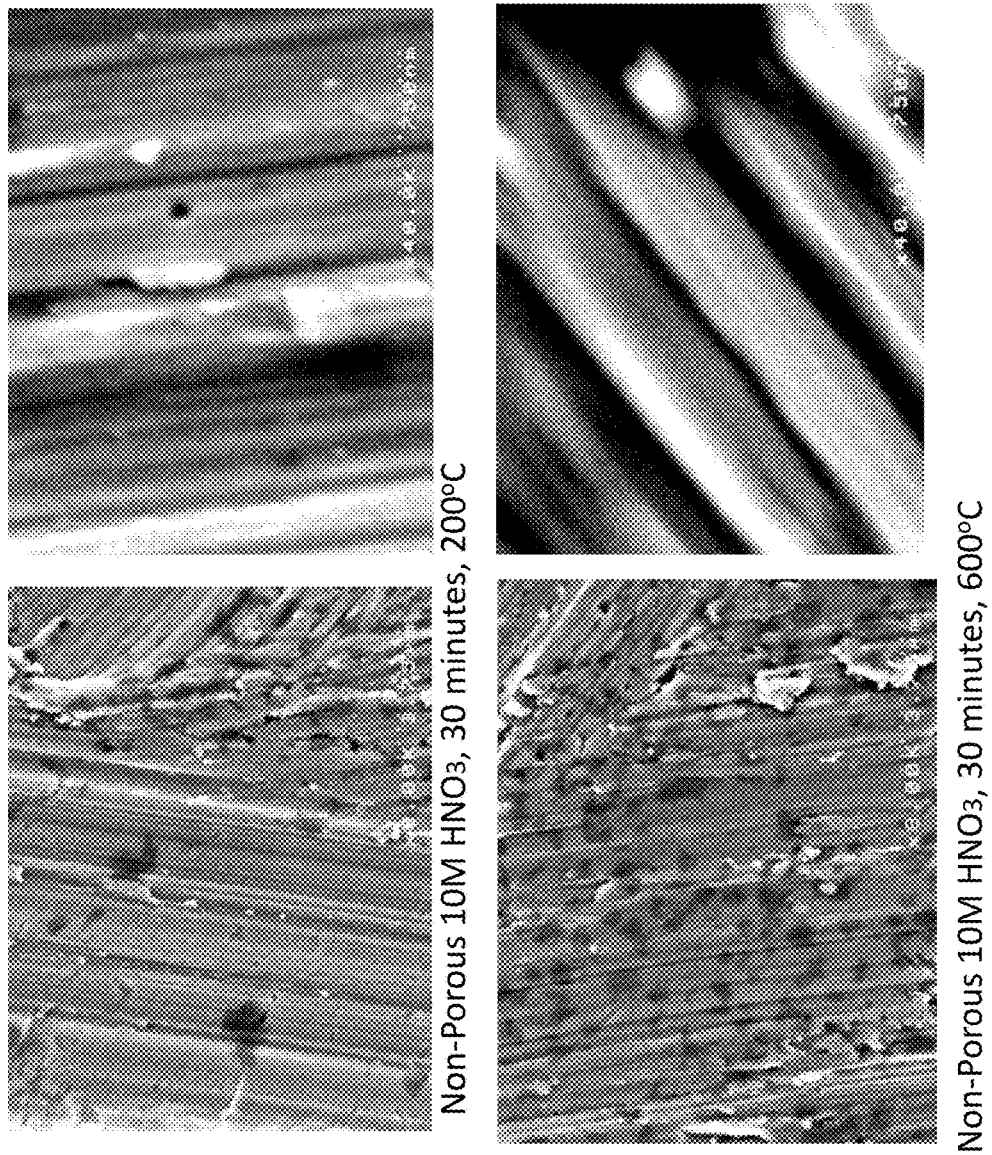
Figure 23:
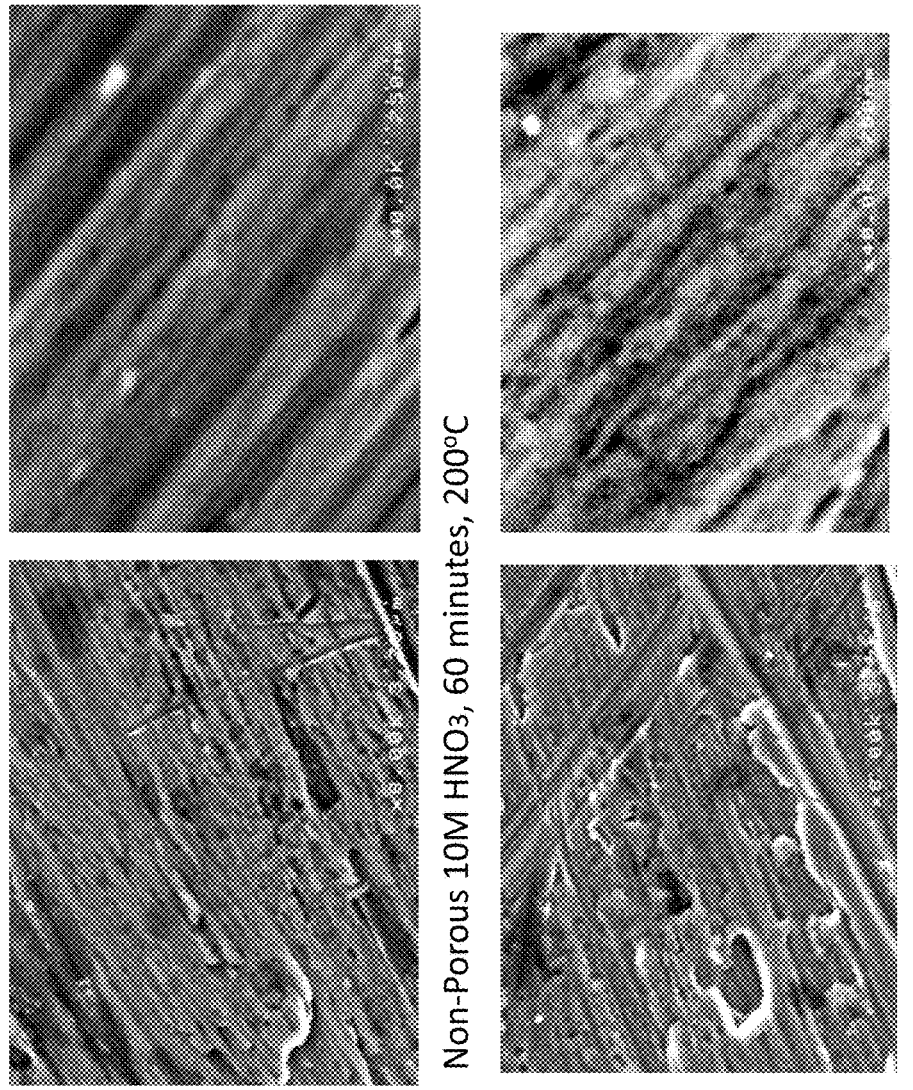
Figure 24:
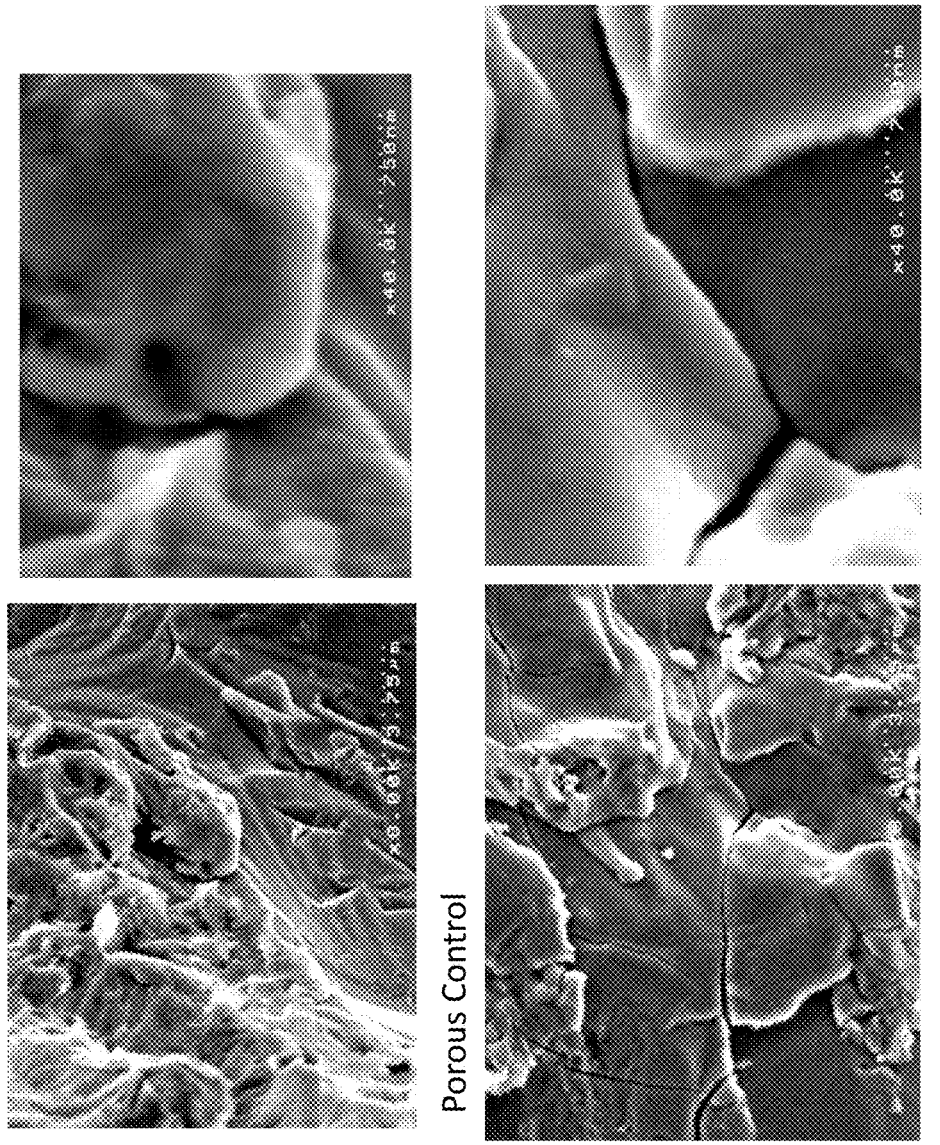
Figure 26:
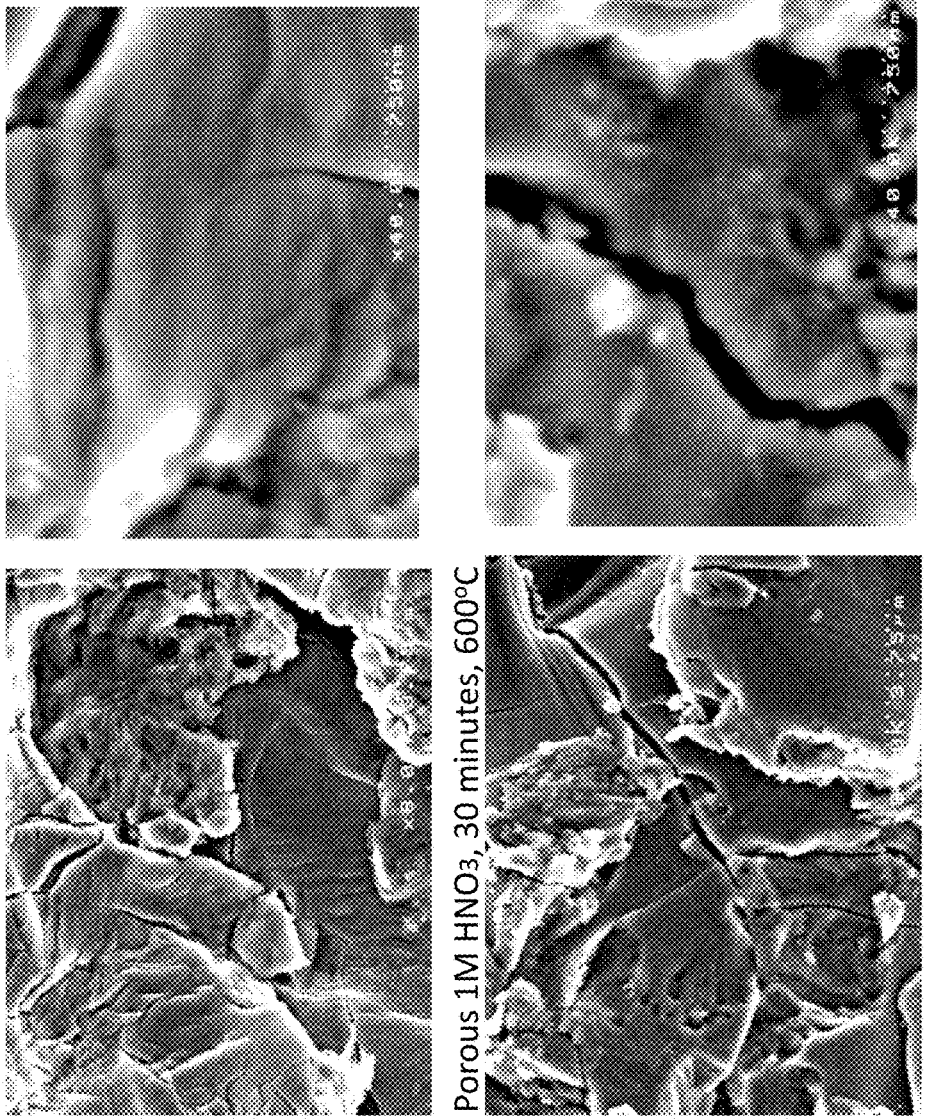
Figure 27:
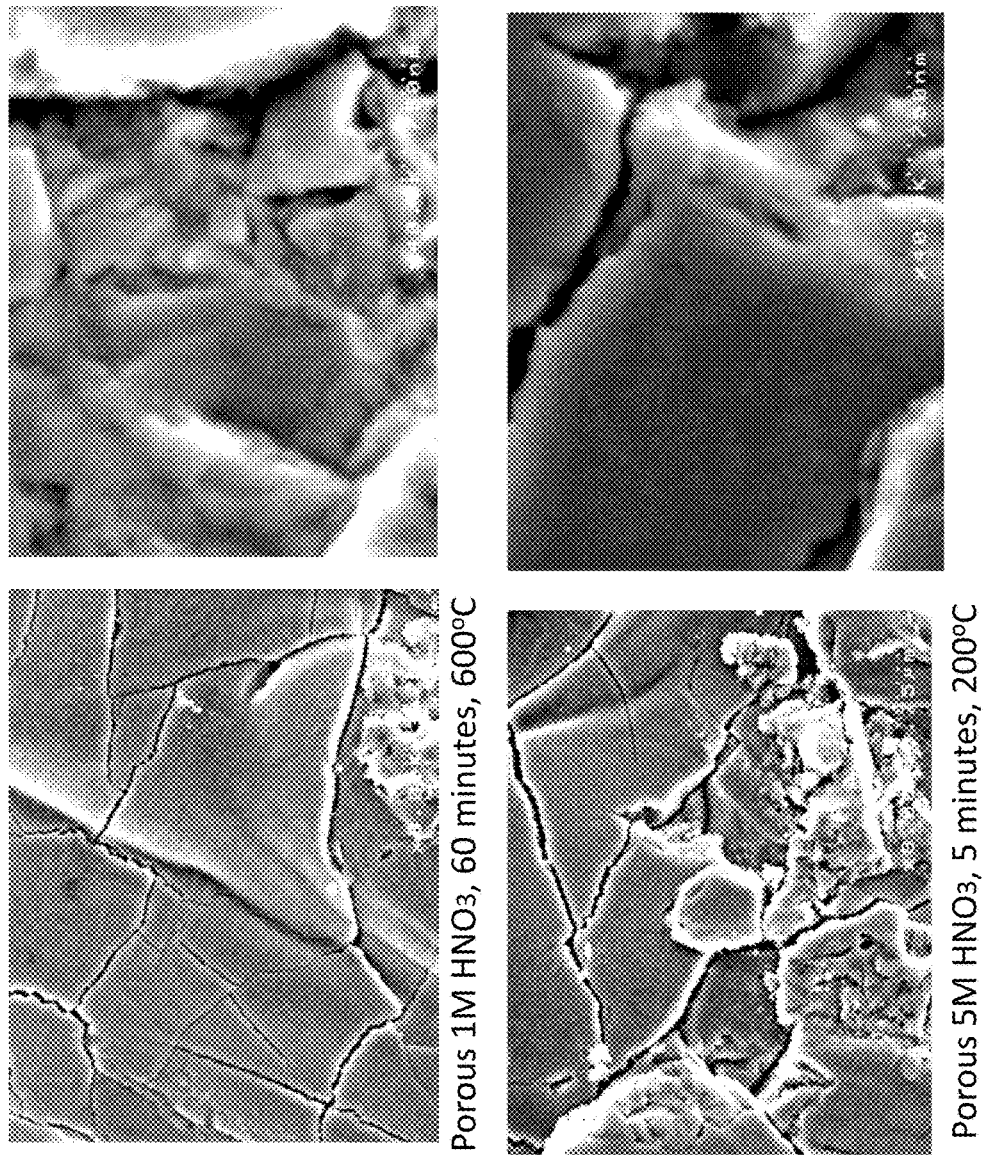
Figure 28:
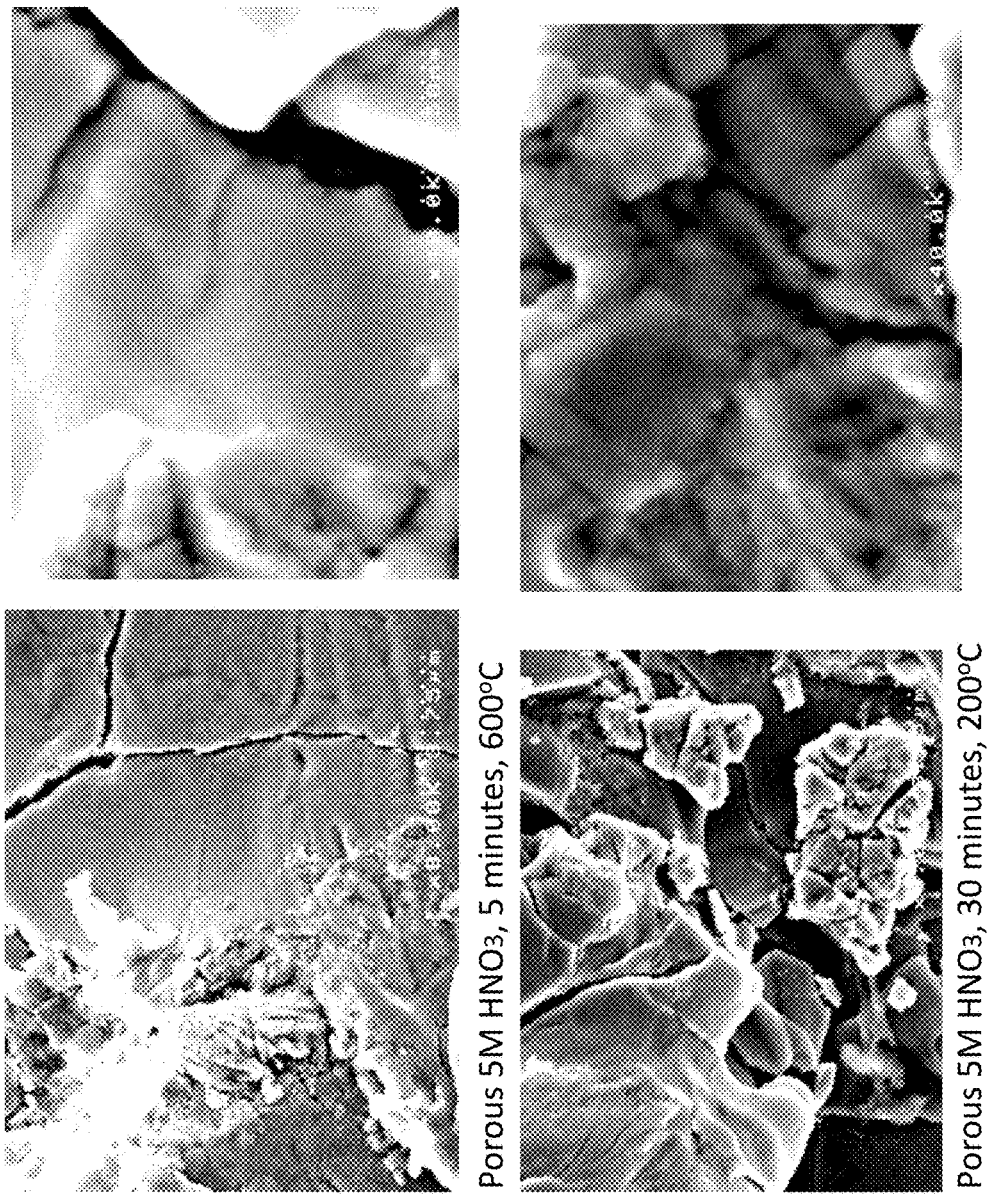
Figure 29:
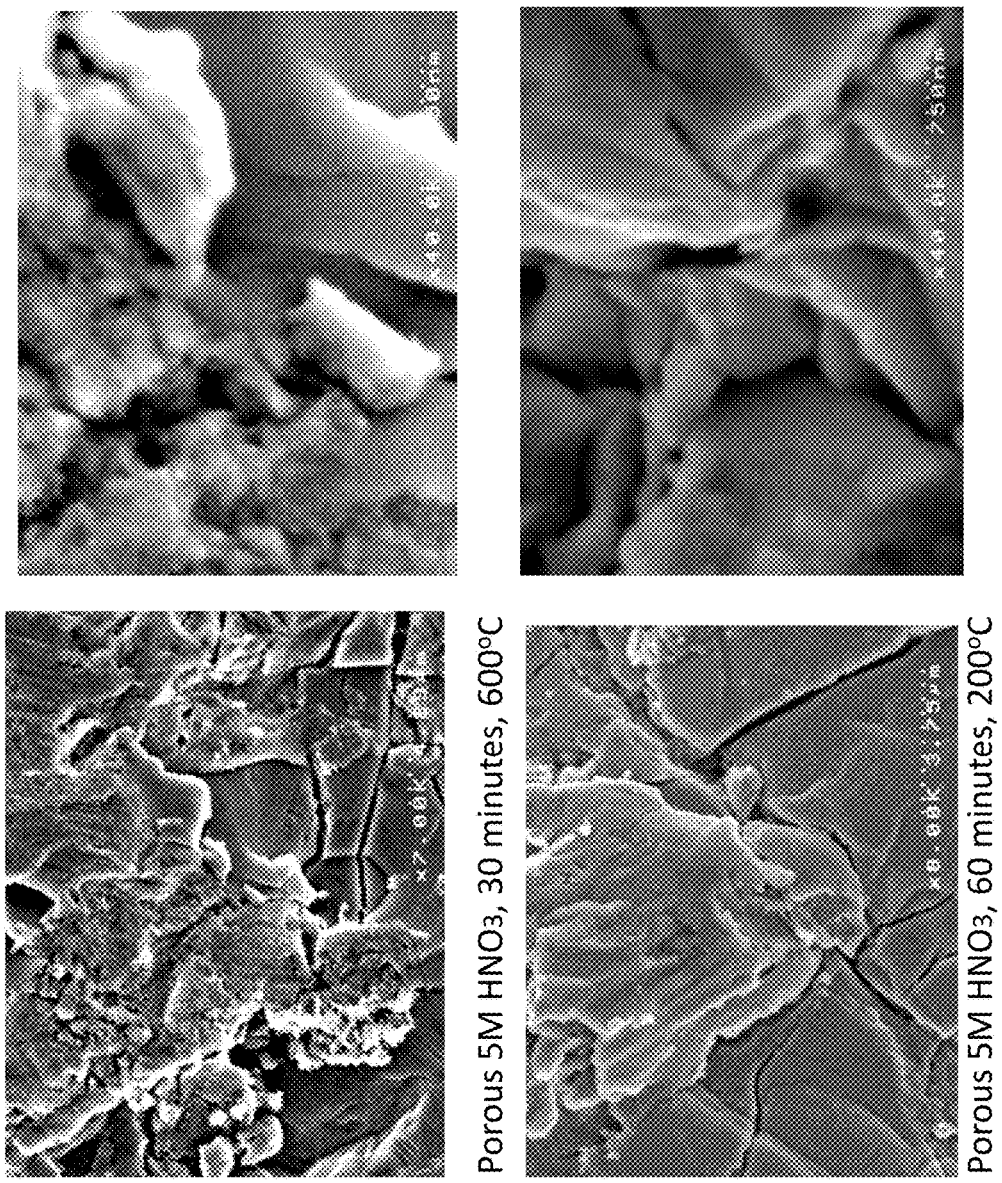
Figure 30:
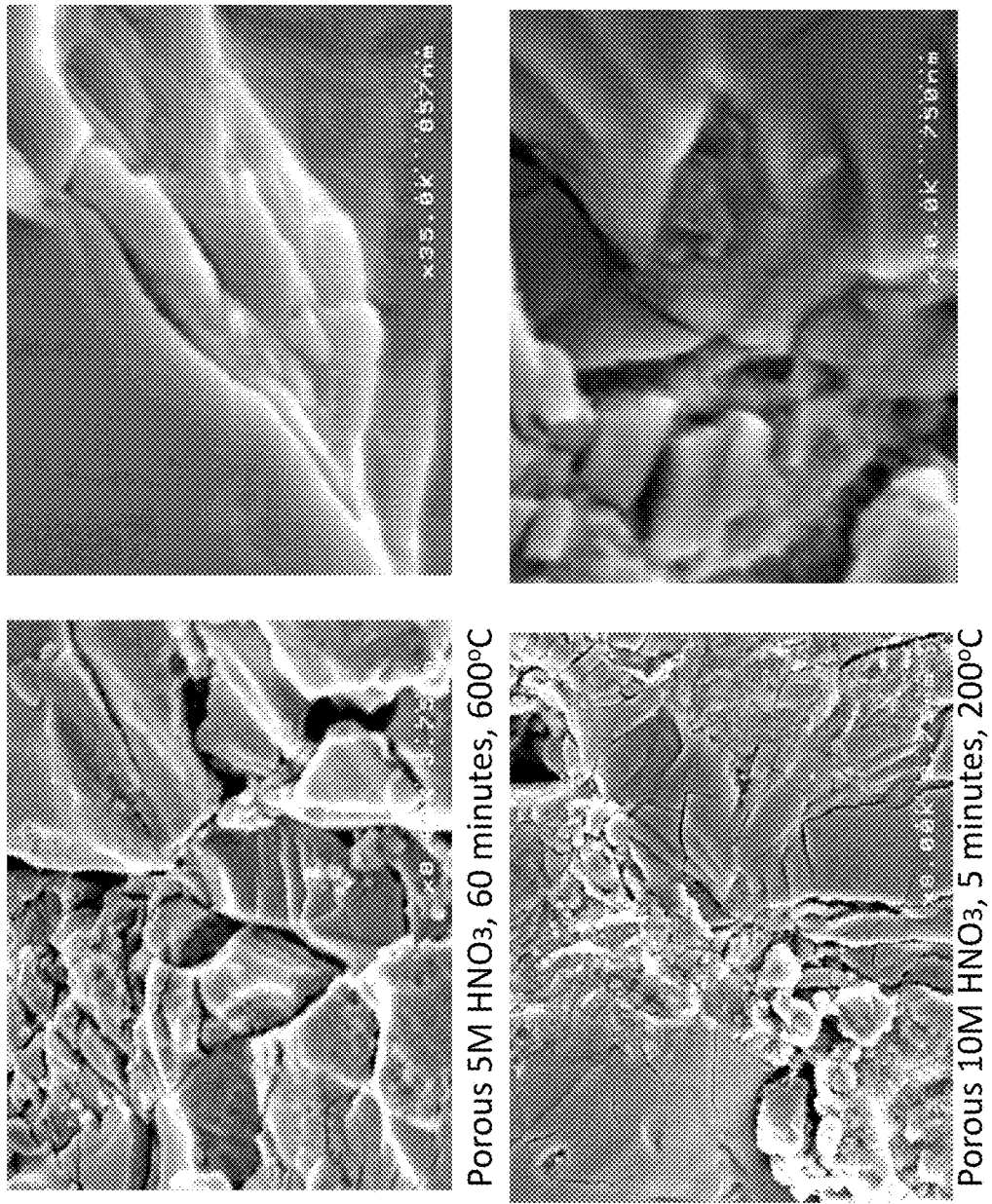
Figure 31:
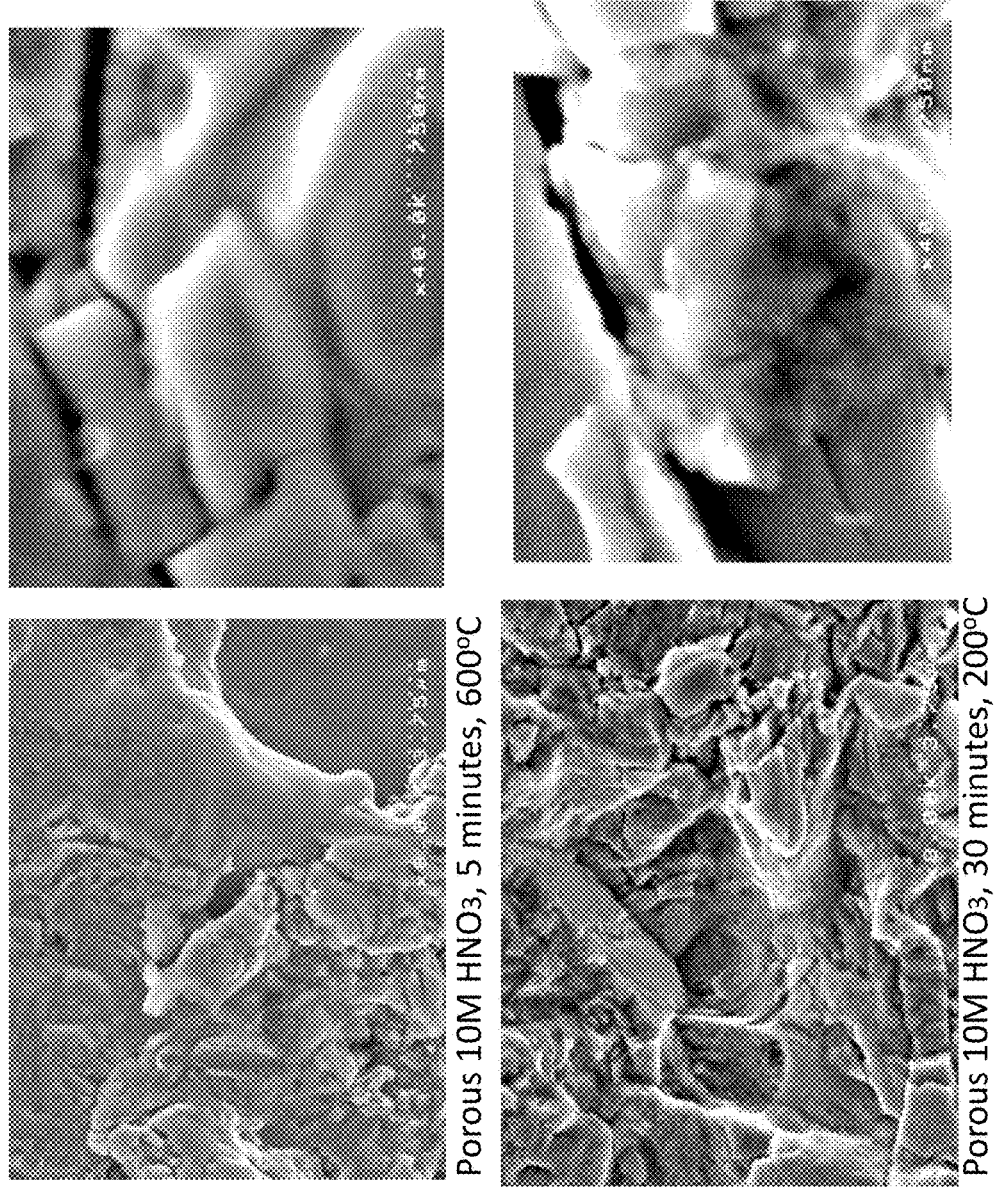
Figure 32:
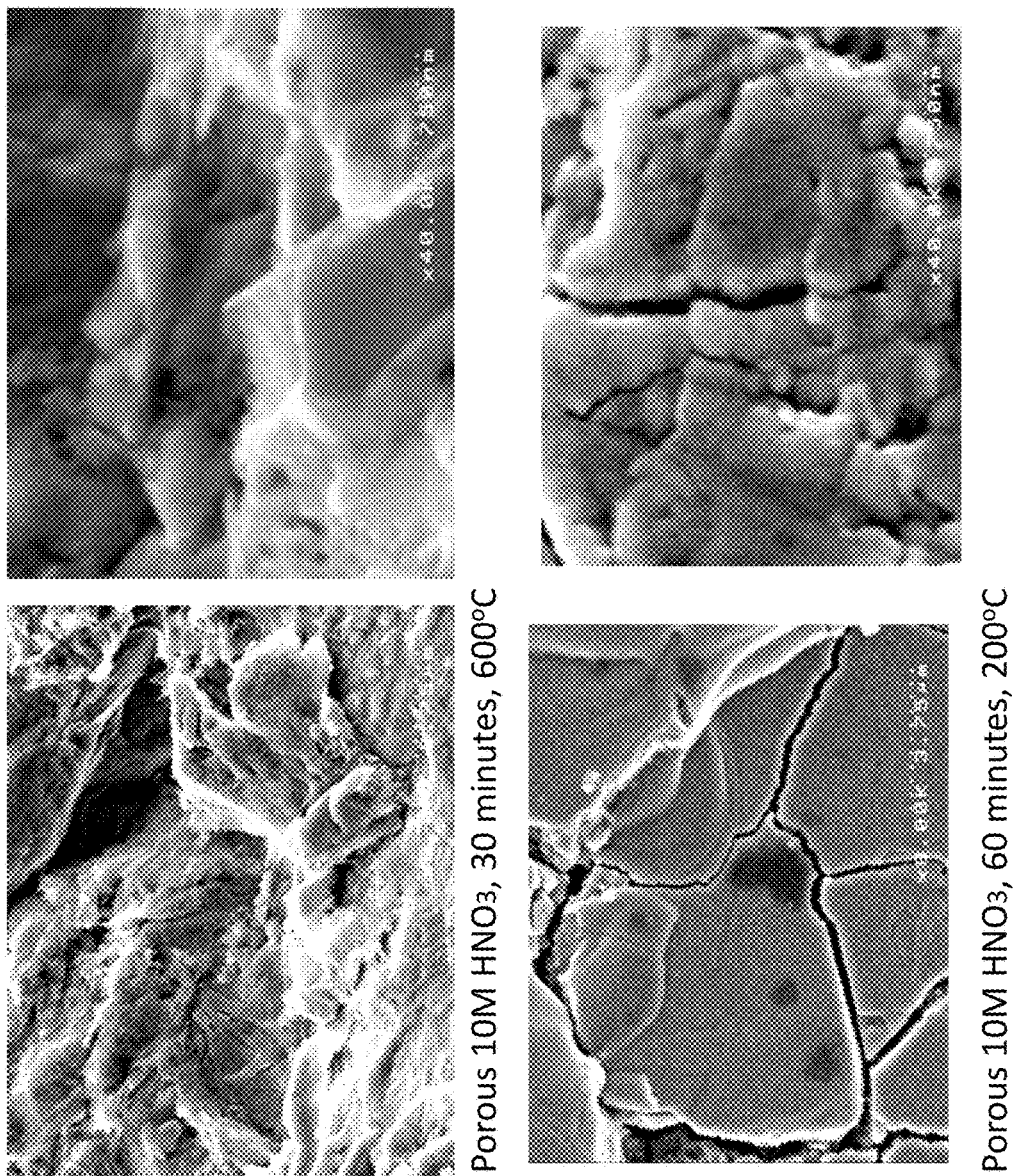
Figure 33:
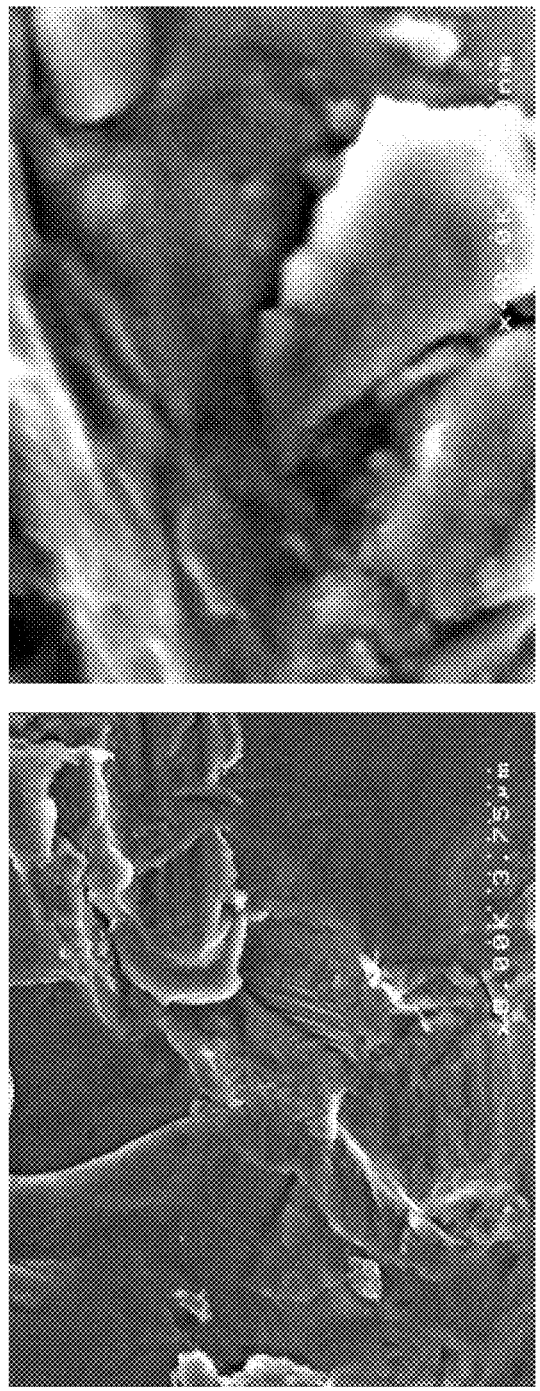
Figure 34:
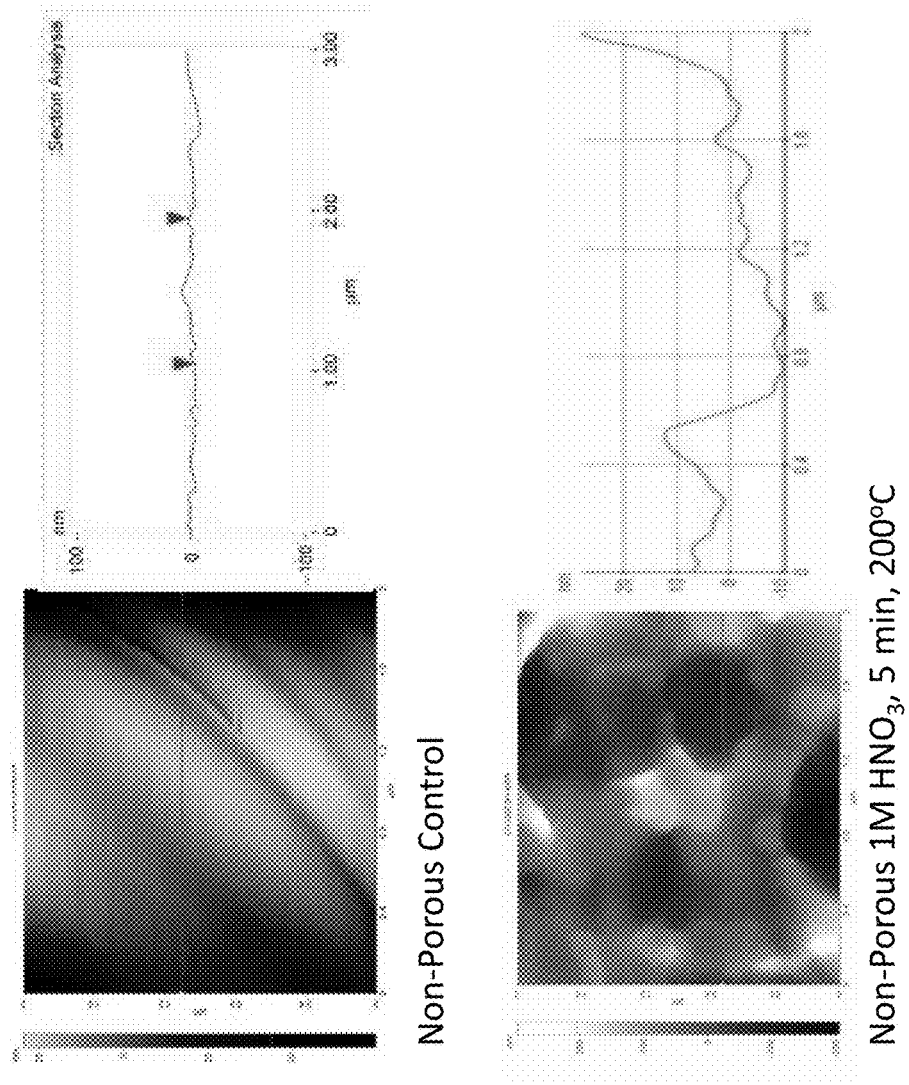
Figure 35:
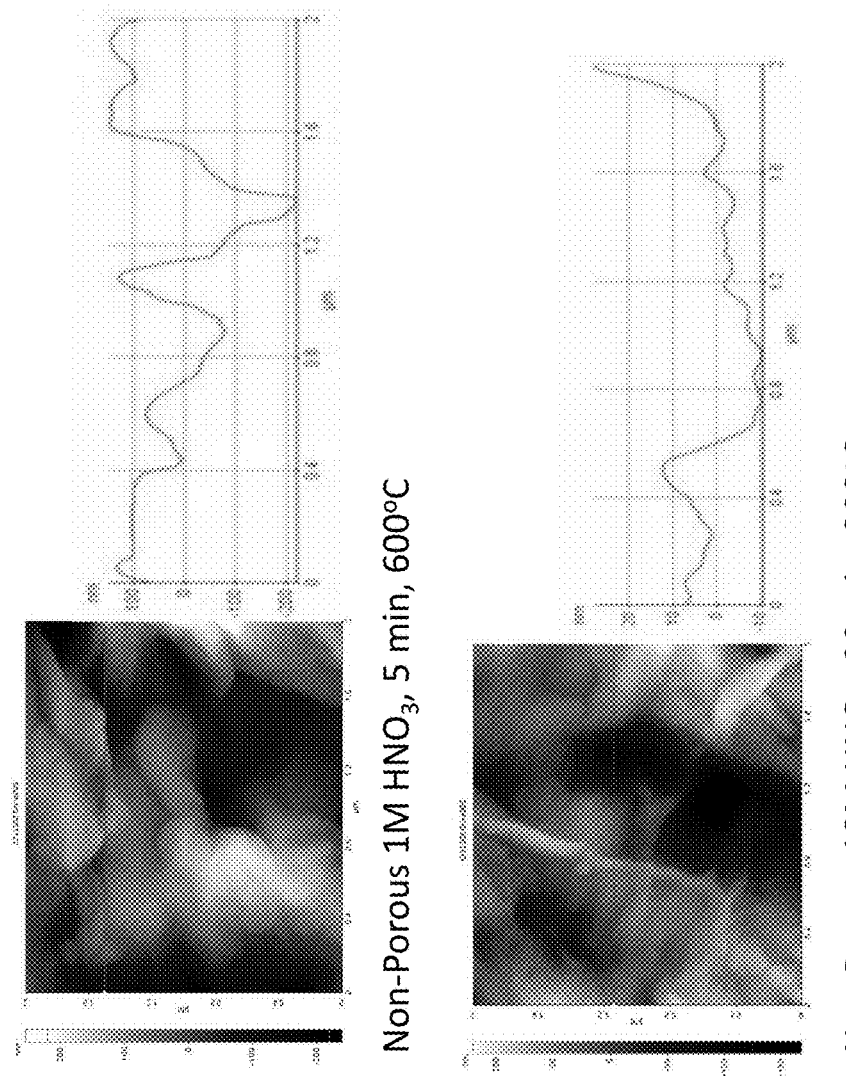
Figure 36:
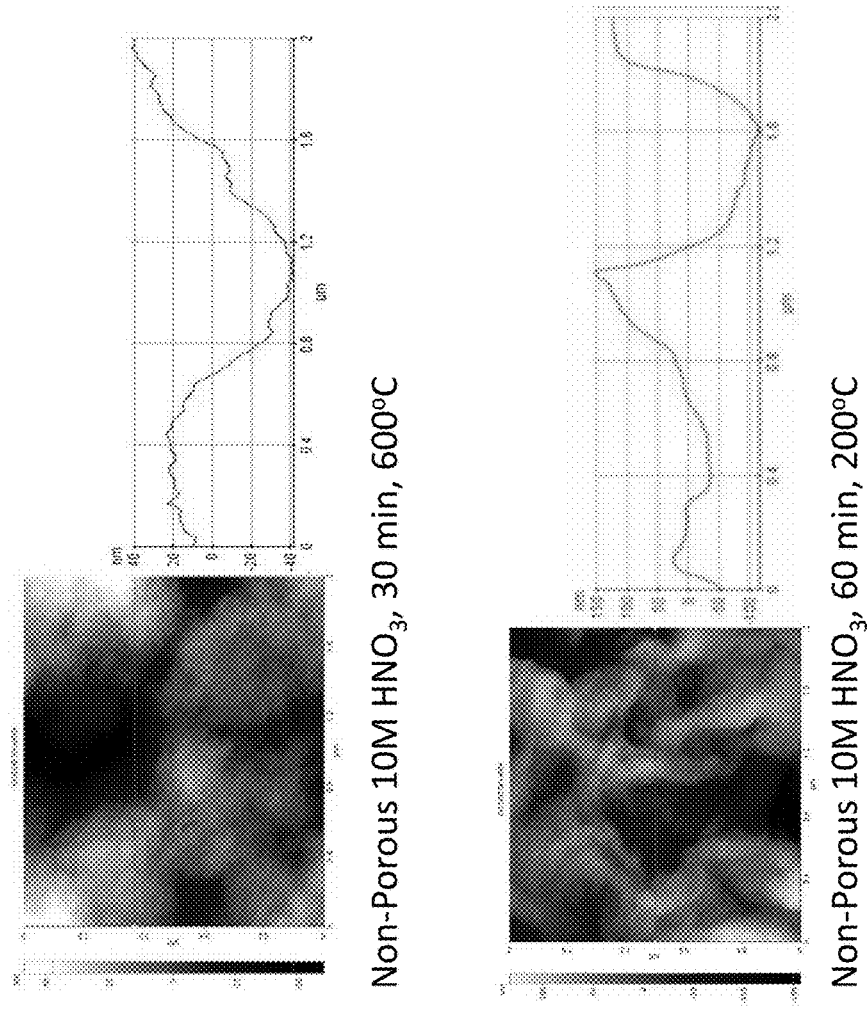
Figure 37:
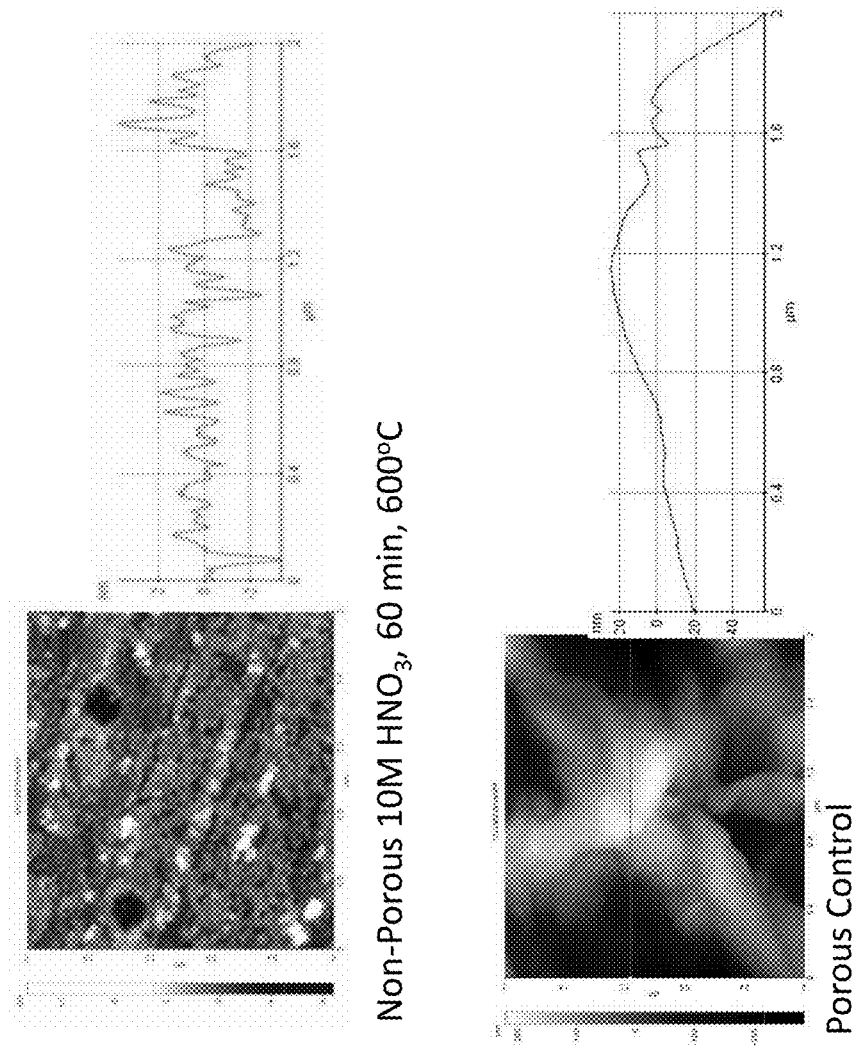
Figure 38:
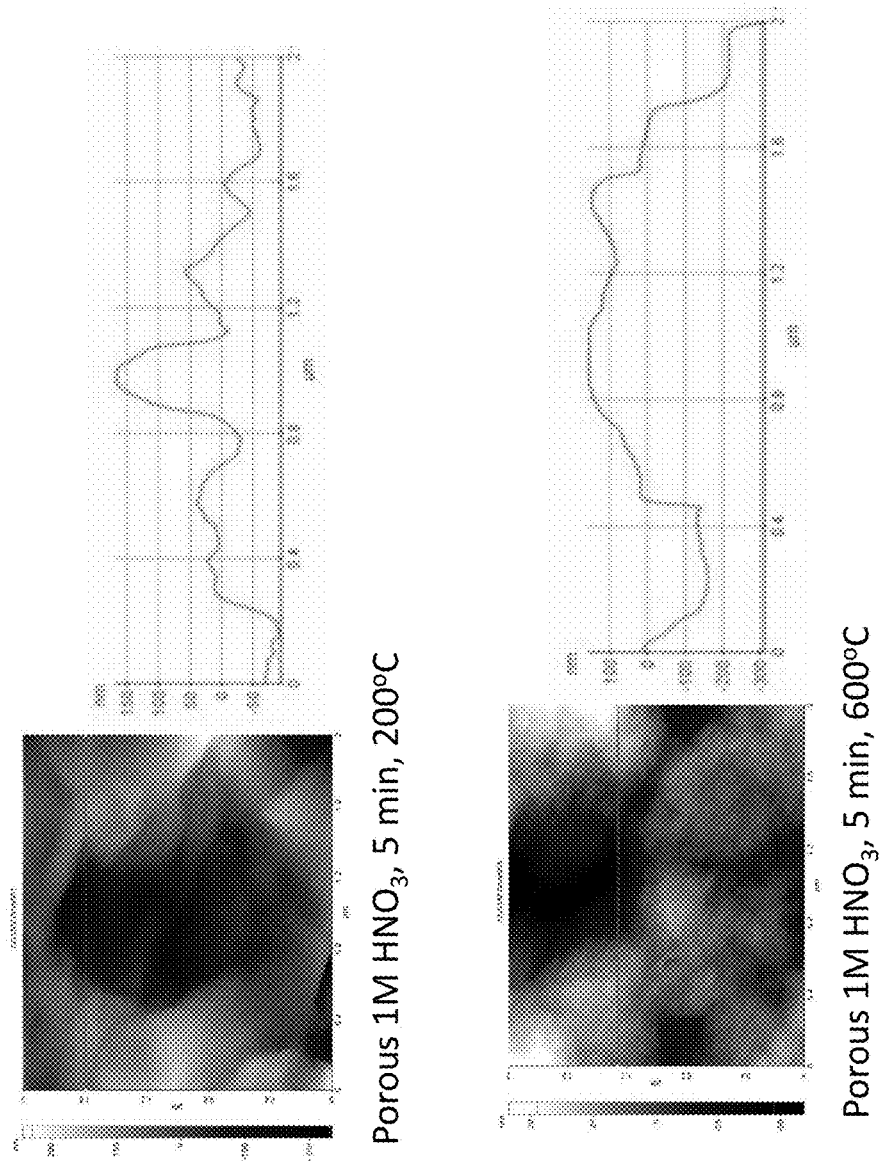
Figure 39:
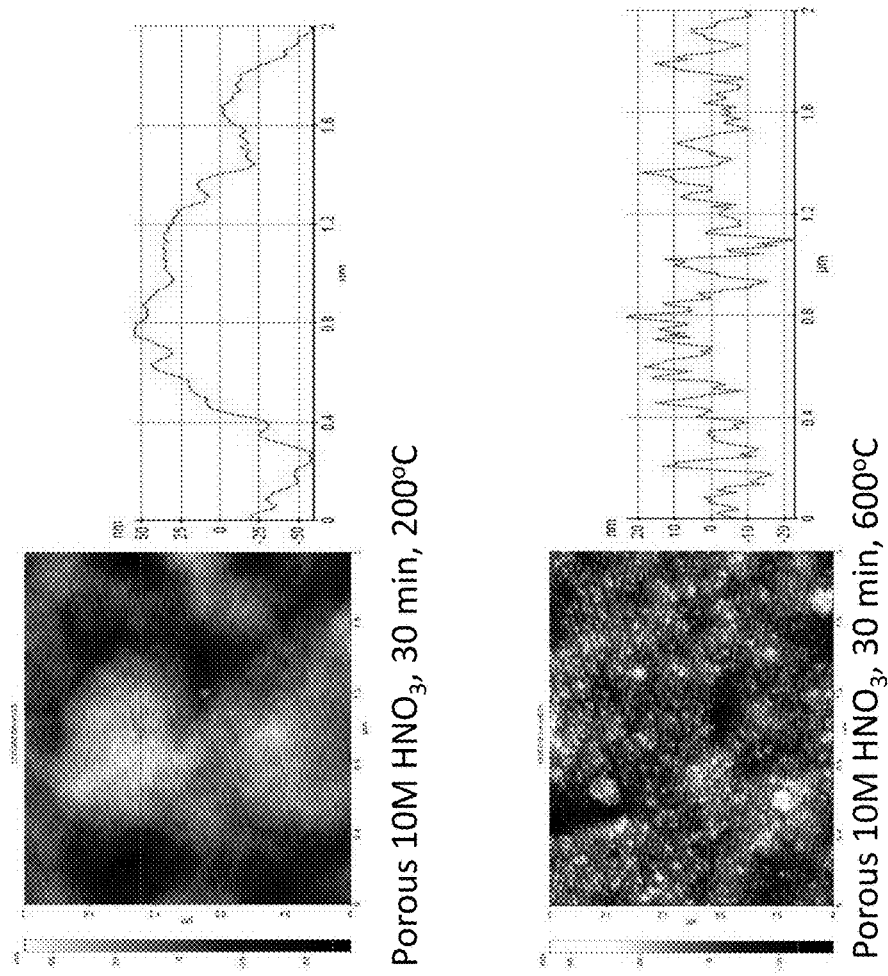
Figure 40:
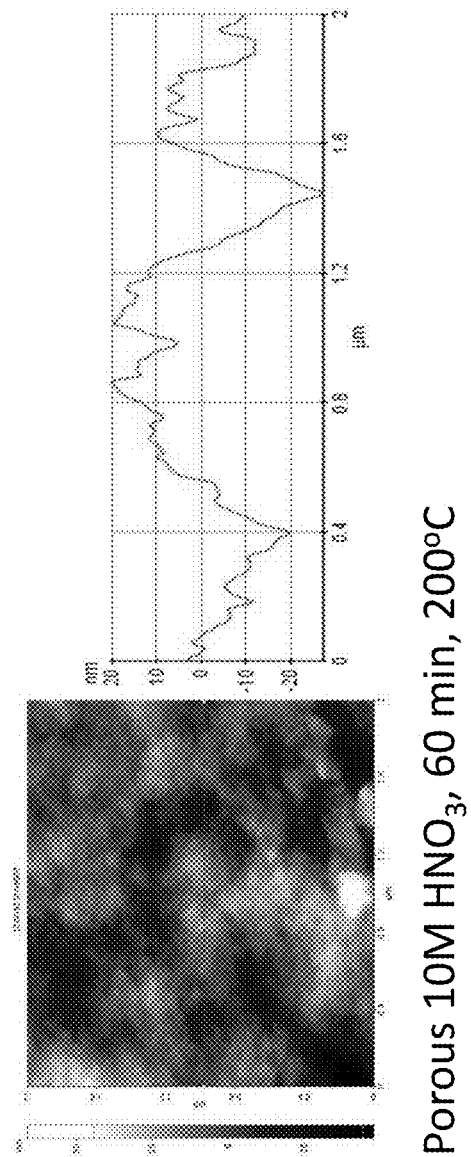
Figure 41:
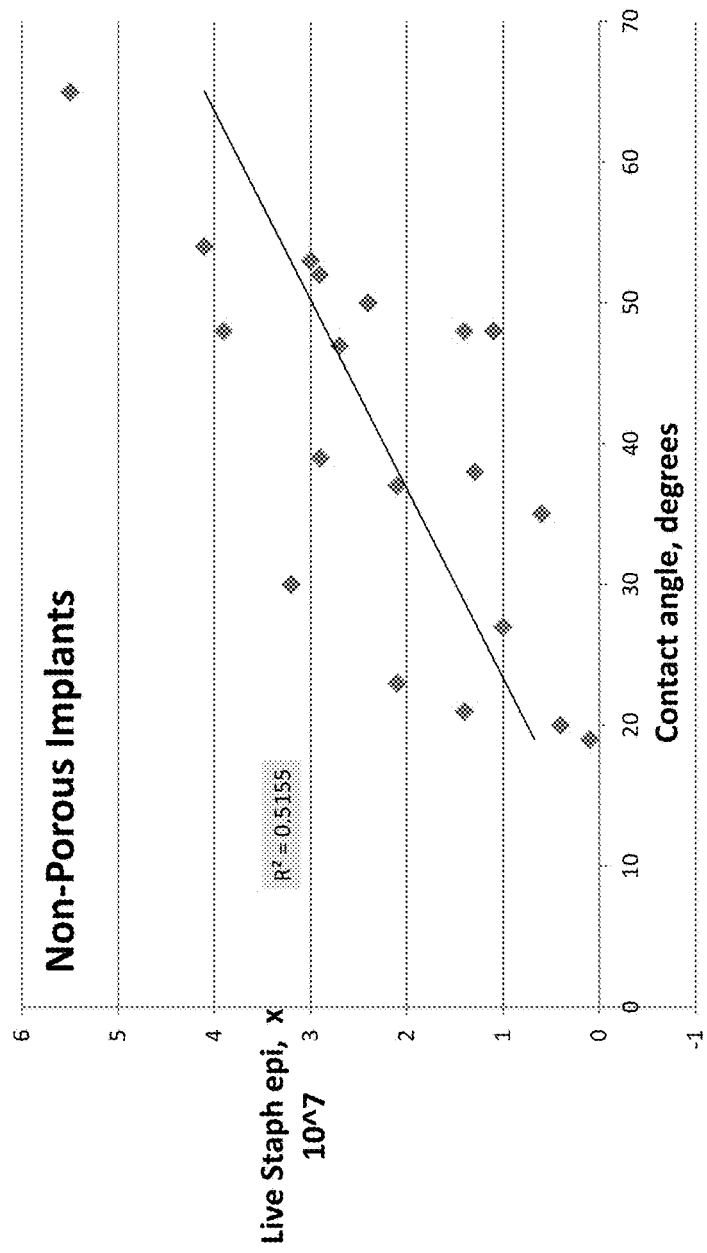
Figure 42:
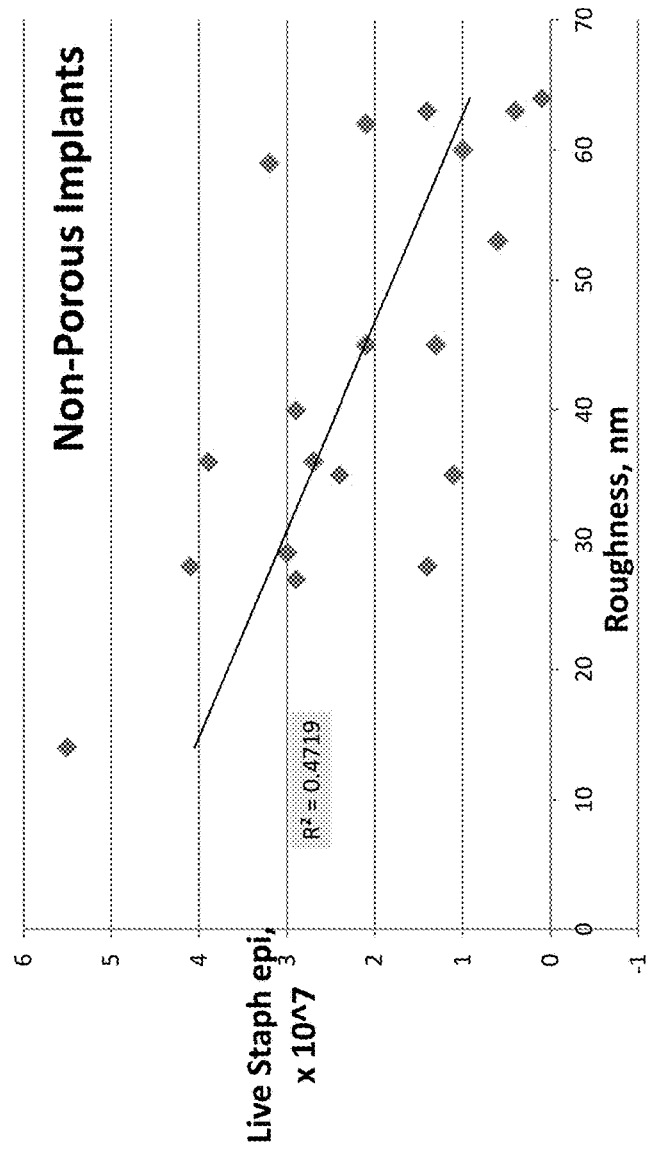
Figure 43:
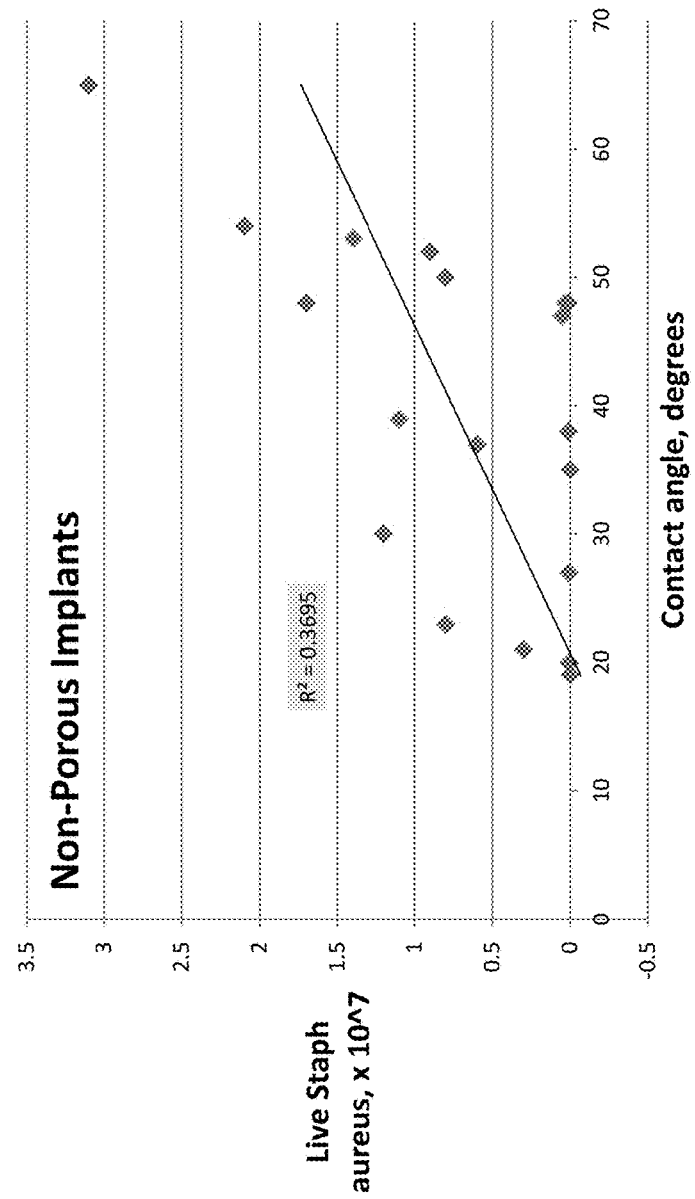
Figure 44:
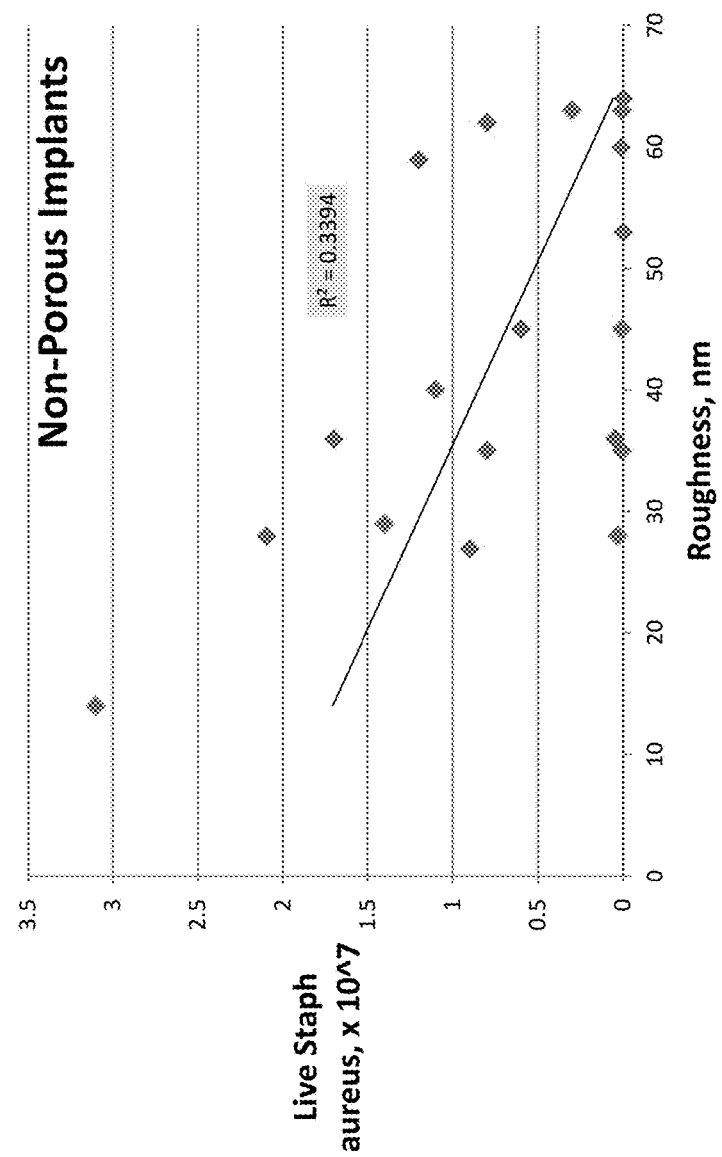
Figure 45:
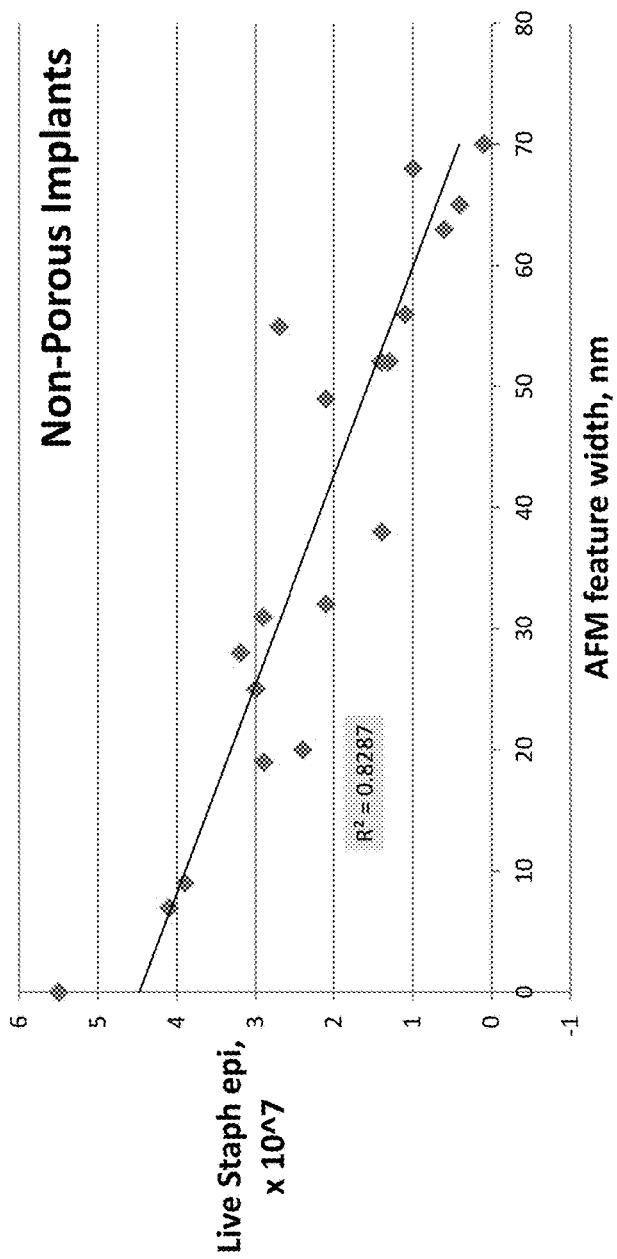
Figure 46:
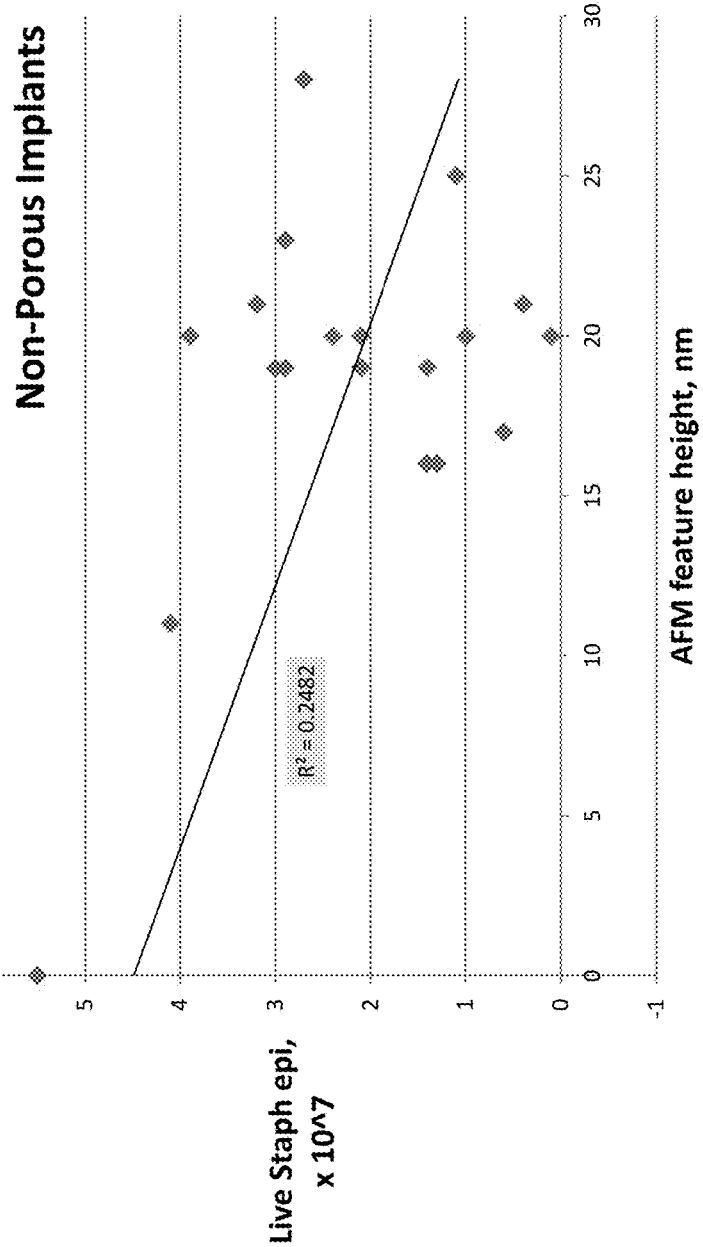
Figure 47:
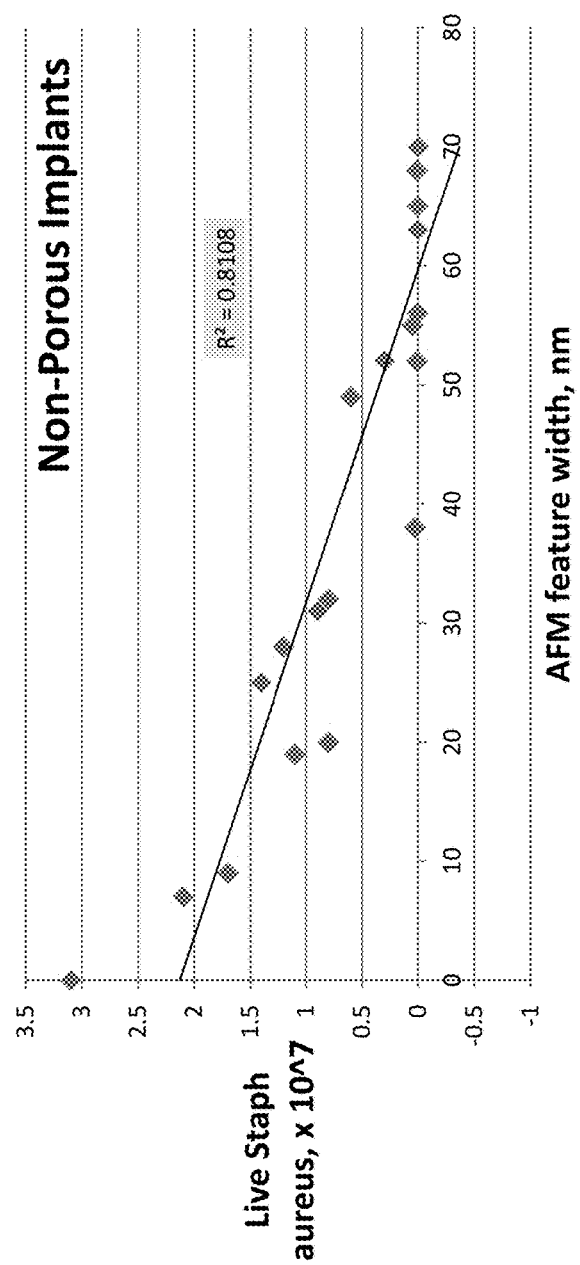
Figure 48:
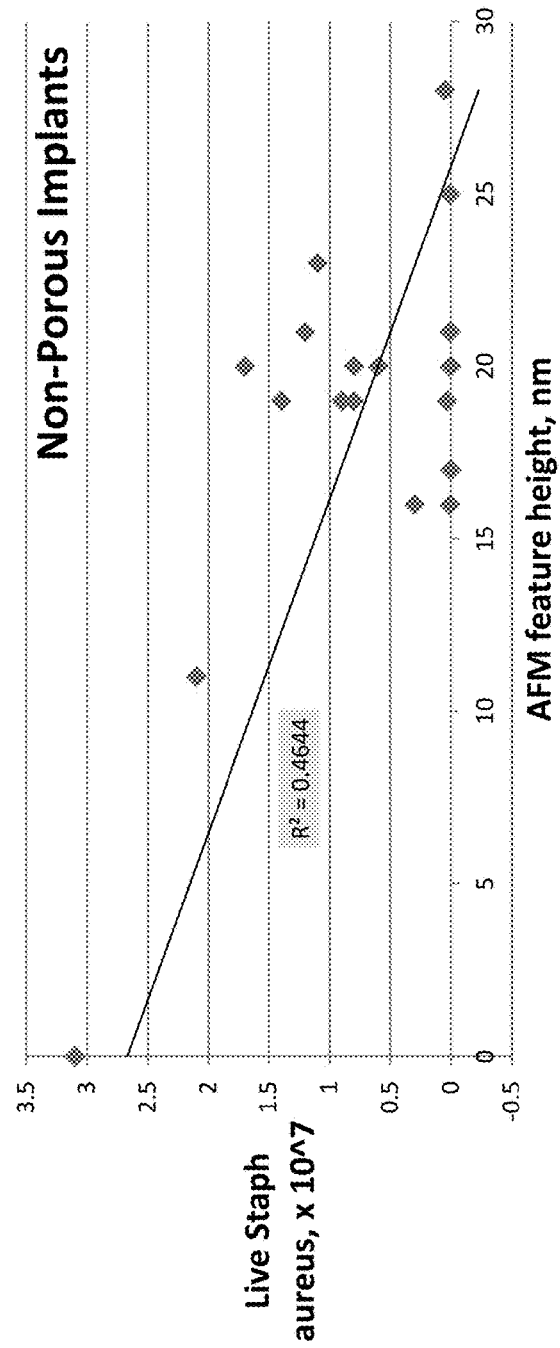
Figure 49:
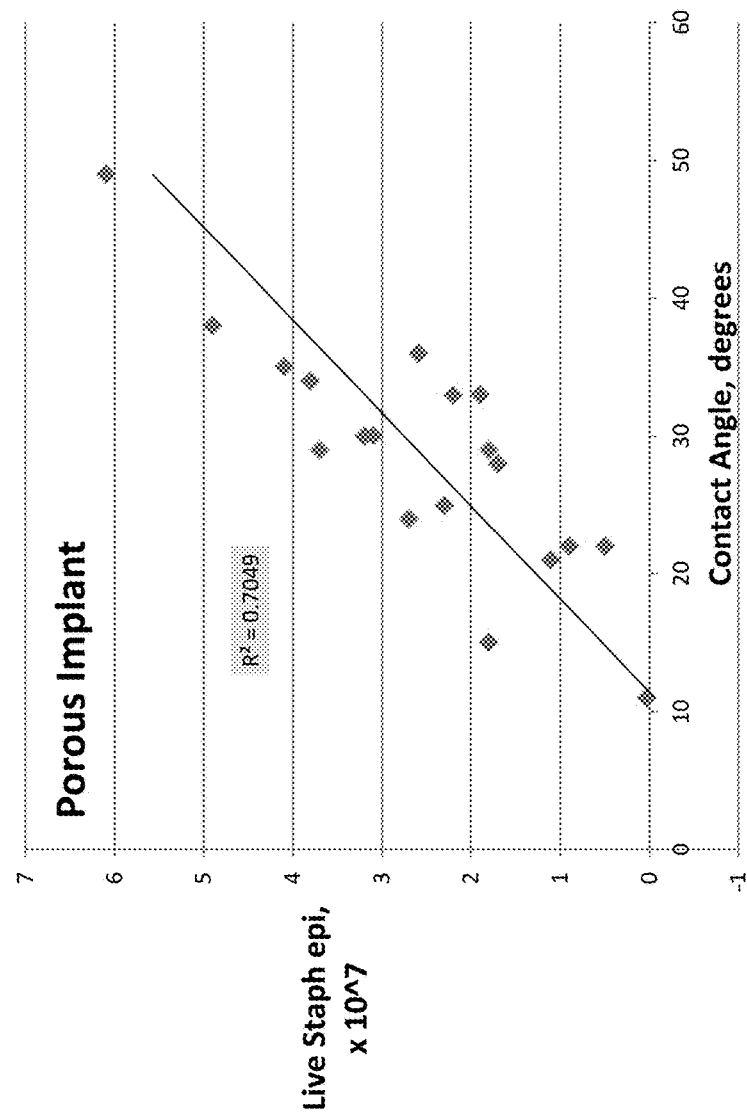
Figure 50:
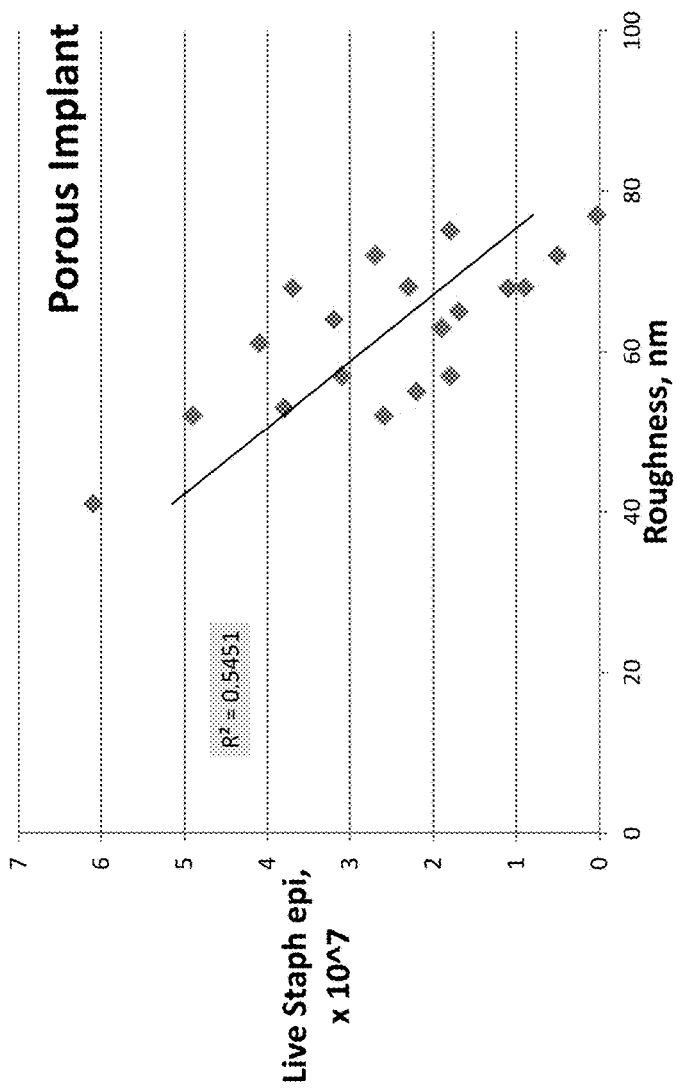
Figure 51:
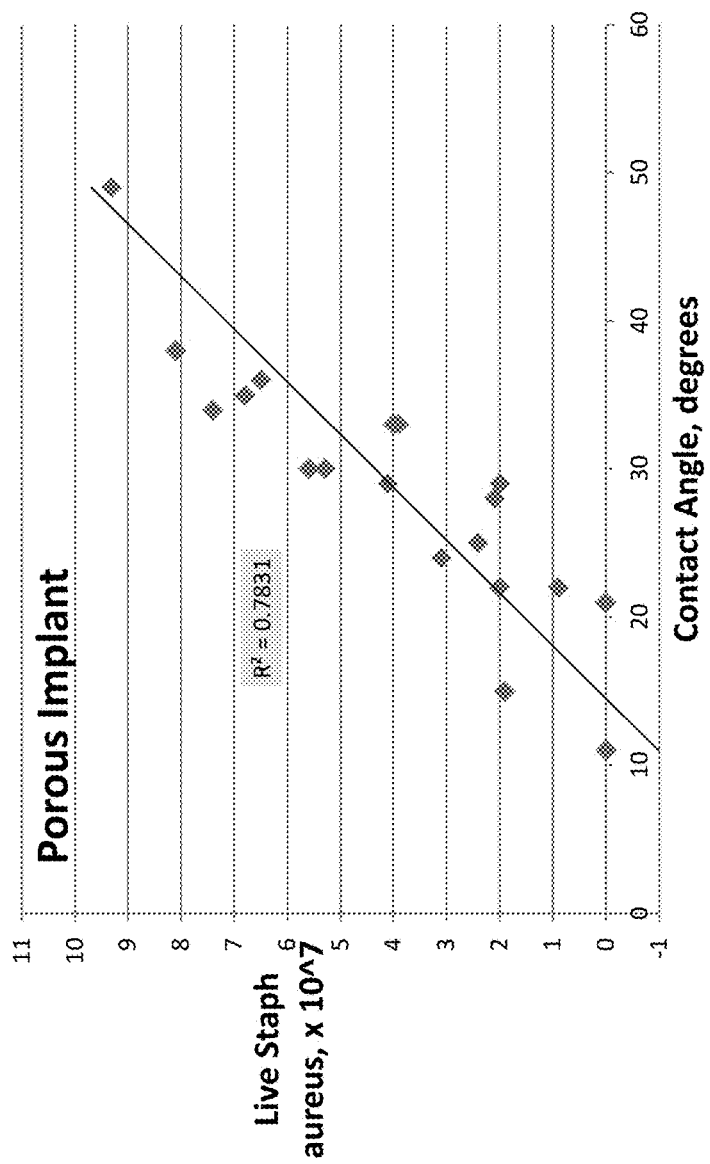
Figure 52:
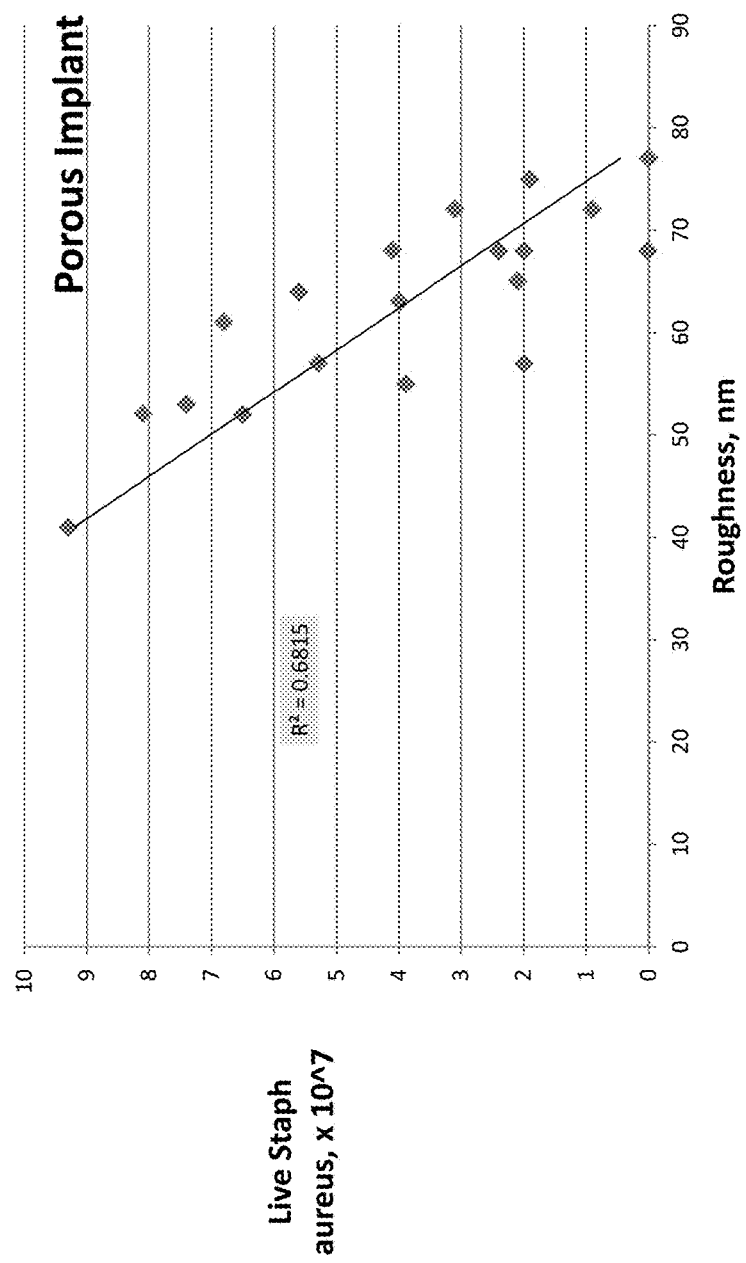
Figure 53:
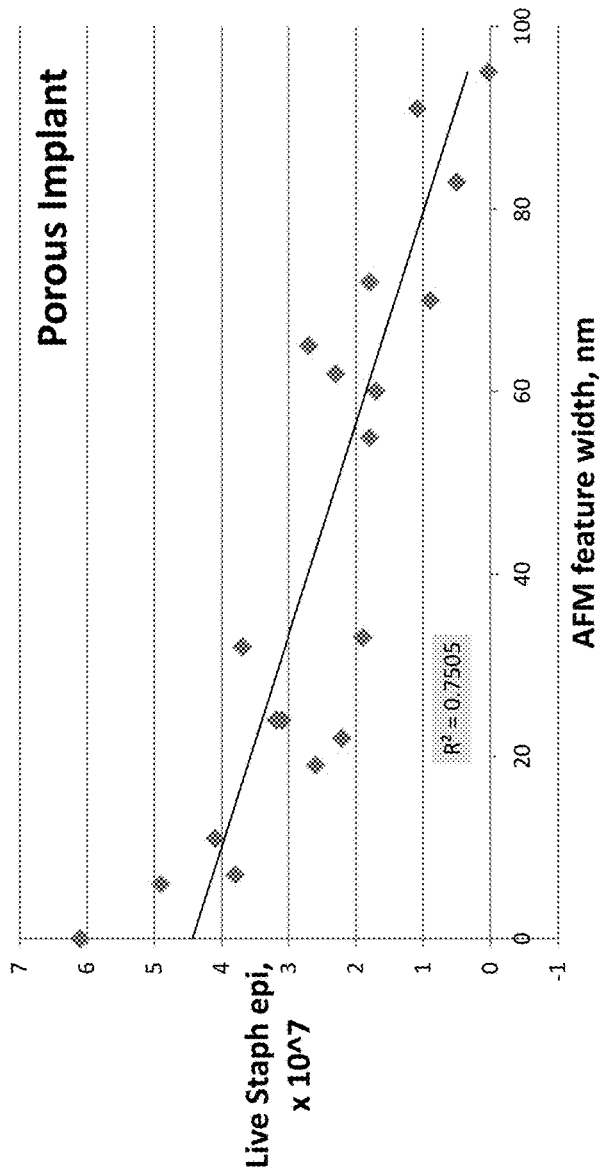
Figure 54:
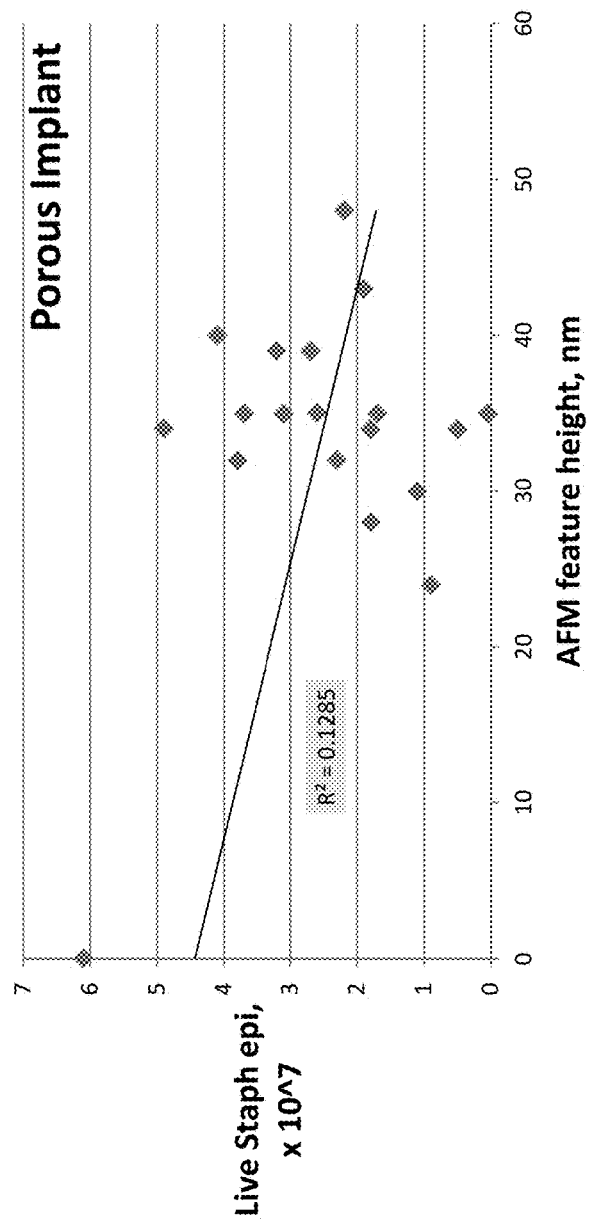
Figure 55:
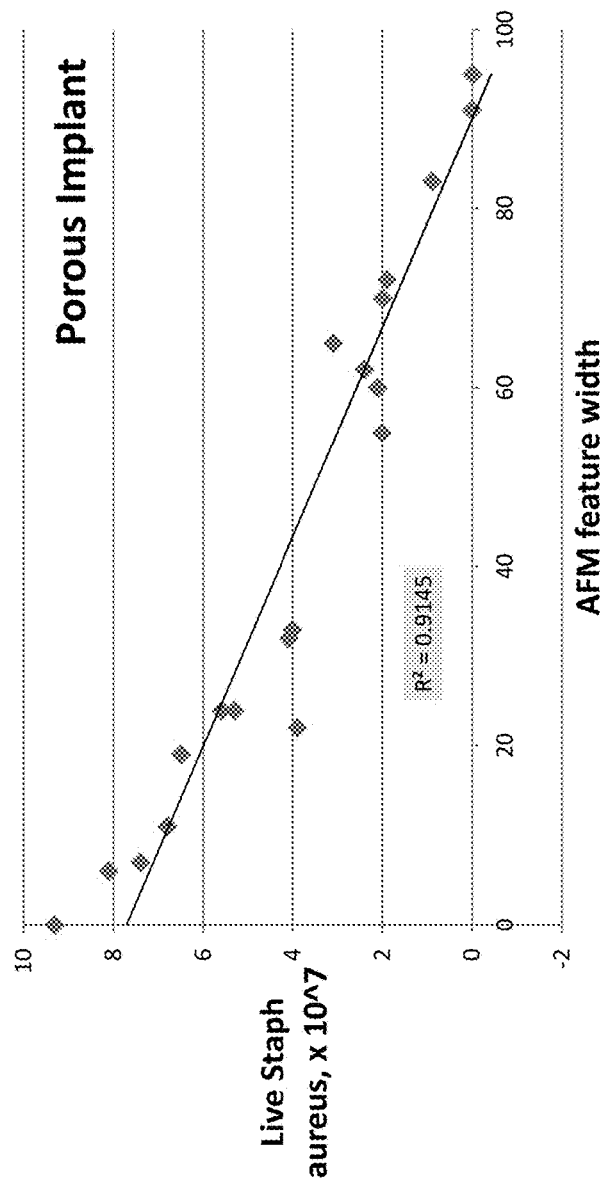
Figure 56:
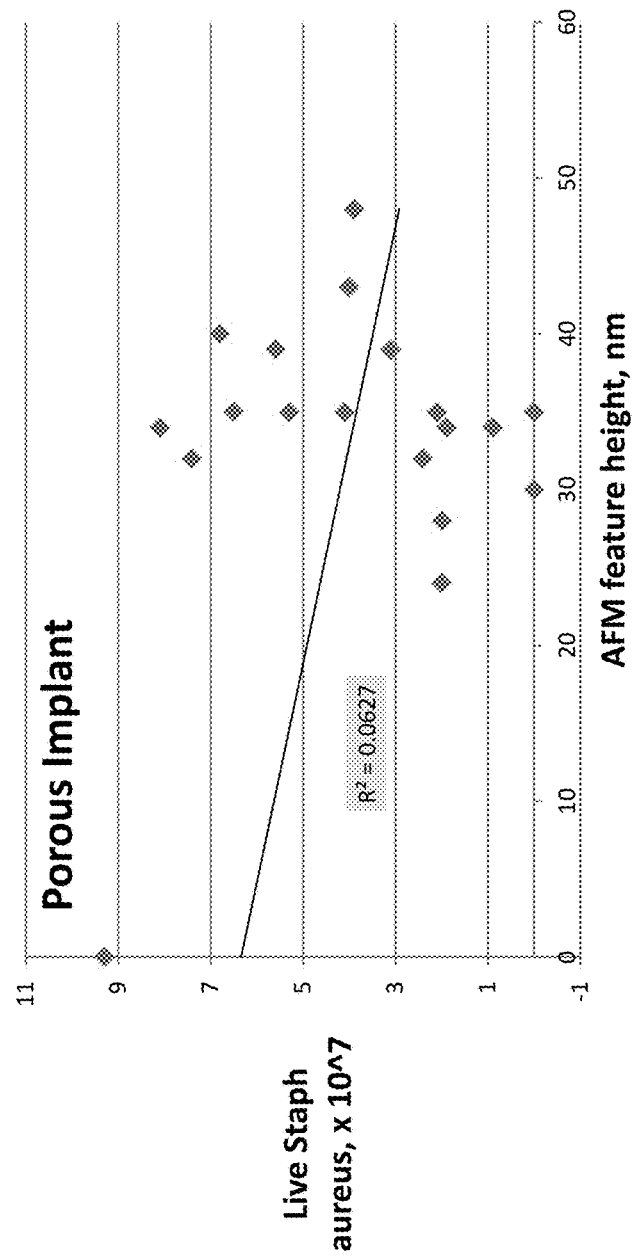

| Concentration of Acid | Time in Acid | Temp of Heating | Cells (×10$^7$) | % Control | FIG. |
|---|---|---|---|---|---|
| Control | — | — | 9.3 | 100% | FIG. 10-12 |
| 1N HNO$_3$ | 5 min | 200° C. | 8.1 | 87% | FIG. 10 |
| 1N HNO$_3$ | 30 min | 200° C. | 7.4 | 80% | FIG. 10 |
| 1N HNO$_3$ | 60 min | 200° C. | 5.3 | 57% | FIG. 10 |
| 1N HNO$_3$ | 5 min | 400° C. | 7.3 | 78% | FIG. 10 |
| 1N HNO$_3$ | 30 min | 400° C. | 5.3 | 57% | FIG. 10 |
| 1N HNO$_3$ | 60 min | 400° C. | 3.9 | 42% | FIG. 10 |
| 1N HNO$_3$ | 5 min | 600° C. | 6.5 | 70% | FIG. 10 |
| 1N HNO$_3$ | 30 min | 600° C. | 3.9 | 42% | FIG. 10 |
| 1N HNO$_3$ | 60 min | 600° C. | 2.0 | 22% | FIG. 10 |
| 5N HNO$_3$ | 5 min | 200° C. | 6.8 | 73% | FIG. 11 |
| 5N HNO$_3$ | 30 min | 200° C. | 5.6 | 60% | FIG. 11 |
| 5N HNO$_3$ | 60 min | 200° C. | 2.4 | 26% | FIG. 11 |
| 5N HNO$_3$ | 5 min | 400° C. | 5.1 | 55% | FIG. 11 |
| 5N HNO$_3$ | 30 min | 400° C. | 3.7 | 40% | FIG. 11 |
| 5N HNO$_3$ | 60 min | 400° C. | 0.8 | 9% | FIG. 11 |
| 5N HNO$_3$ | 5 min | 600° C. | 4.0 | 43% | FIG. 11 |

TABLE 4-continued

Growth of *Staphyloccocus aureus* on
Porous Nano-Modified Titanium Implants

| Concentration of Acid | Time in Acid | Temp of Heating | Cells (×10⁷) | % Control | FIG. |
|---|---|---|---|---|---|
| 5N HNO₃ | 30 min | 600° C. | 2.1 | 23% | FIG. 11 |
| 5N HNO₃ | 60 min | 600° C. | 0.01 | 0.1% | FIG. 11 |
| 10N HNO₃ | 5 min | 200° C. | 4.1 | 44% | FIG. 12 |
| 10N HNO₃ | 30 min | 200° C. | 3.1 | 33% | FIG. 12 |
| 10N HNO₃ | 60 min | 200° C. | 1.9 | 20% | FIG. 12 |
| 10N HNO₃ | 5 min | 400° C. | 3.2 | 34% | FIG. 12 |
| 10N HNO₃ | 30 min | 400° C. | 1.9 | 20% | FIG. 12 |
| 10N HNO₃ | 60 min | 400° C. | 0.1 | 1% | FIG. 12 |
| 10N HNO₃ | 5 min | 600° C. | 2.0 | 22% | FIG. 12 |
| 10N HNO₃ | 30 min | 600° C. | 0.9 | 10% | FIG. 12 |
| 10N HNO₃ | 60 min | 600° C. | 0.0009 | 0.01% | FIG. 12 |

Example 2

Material Characterization

The nano-modified implants prepared above were characterized for: 1) surface roughness using Scanning Electron Microscopy (SEM); 2) chemistry using X-ray photoelectron spectroscopy (XPS); and 3) surface energy (wettability) using contact angles following well established methods. For contact angle analysis, a known drop of water (10 microliters) was placed on the surfaces at room temperature and the angle it makes with the surface determined using a video camera.

Surface Roughness was determined using an atomic force microscope which drags a cantilever over the surface of a material to measure the roughness of the surface.

Representative SEM images are illustrated in FIGS. 5-12. These results demonstrate significantly greater roughness at the nanoscale level with increasing acid treatment times, increasing acid concentrations, and increasing heating temperatures.

Additional surface roughness measurements were obtained using a Parks Scientific NX-10 Atomic Force Microscope (AFM) (Suwon, Korea) to scan the nano-modified implants. Each implant was analyzed in ambient conditions under non-contact mode using a silicone ultrasharp cantilever (Park Systems Non-contact Cantilever). The AFM tip had a radius of curvature less than 7 nm and had a backside aluminum reflex coating approximately 30 nm thick. Tapping mode was used at 324 kHz at a scan rate of 0.5 Hz. Surface width and length were measured directly off of the computer software. For a select set of samples, image analysis software (XEI) was used to generate AFM micrographs and line scans. Representative illustrations are demonstrated in FIGS. 13-19.

A summary of the results of the surface roughness studies are summarized in Tables 5 and 6 below.

TABLE 5

AFM surface Roughness of Non-Porous Nano-Modified Implants

| Concentration | Soaking Time (minutes) | Temperature (deg. C.) | Roughness (nanometers) | Average AFM feature width (nanometers) | Average AFM feature height (nanometers) |
|---|---|---|---|---|---|
| Non-Porous Control | N/A | RT | 14 | 0 | 0 |
| 1M HNO₃ | 5 | 200 | 28 | 7 | 11 |
| 1M HNO₃ | 5 | 600 | 27 | 31 | 19 |
| 1M HNO₃ | 30 | 200 | 29 | 25 | 19 |
| 1M HNO₃ | 30 | 600 | 28 | 38 | 19 |
| 1M HNO₃ | 60 | 200 | 35 | 20 | 20 |
| 1M HNO₃ | 60 | 600 | 35 | 56 | 25 |
| 5M HNO₃ | 5 | 200 | 36 | 9 | 20 |
| 5M HNO₃ | 5 | 600 | 36 | 55 | 28 |
| 5M HNO₃ | 30 | 200 | 40 | 19 | 23 |
| 5M HNO₃ | 30 | 600 | 45 | 52 | 16 |
| 5M HNO₃ | 60 | 200 | 45 | 49 | 20 |
| 5M HNO₃ | 60 | 600 | 53 | 63 | 17 |
| 10M HNO₃ | 5 | 200 | 59 | 28 | 21 |
| 10M HNO₃ | 5 | 600 | 60 | 68 | 20 |
| 10M HNO₃ | 30 | 200 | 62 | 32 | 19 |
| 10M HNO₃ | 30 | 600 | 63 | 65 | 21 |
| 10M HNO₃ | 60 | 200 | 63 | 52 | 16 |
| 10M HNO₃ | 60 | 600 | 64 | 70 | 20 |

TABLE 6

AFM surface Roughness of Porous Nano-Modified Implants

| Concentration | Soaking Time (minutes) | Temperature (deg. C.) | Average Roughness (nanometers) | Average AFM feature width (nanometers) | Average AFM feature height (nanometers) |
|---|---|---|---|---|---|
| Porous Control | N/A | RT | 41 | 0 | 0 |
| 1M HNO₃ | 5 | 200 | 52 | 6 | 34 |
| 1M HNO₃ | 5 | 600 | 52 | 19 | 35 |
| 1M HNO₃ | 30 | 200 | 53 | 7 | 32 |
| 1M HNO₃ | 30 | 600 | 55 | 22 | 48 |
| 1M HNO₃ | 60 | 200 | 57 | 24 | 35 |
| 1M HNO₃ | 60 | 600 | 57 | 55 | 28 |
| 5M HNO₃ | 5 | 200 | 61 | 11 | 40 |
| 5M HNO₃ | 5 | 600 | 63 | 33 | 43 |
| 5M HNO₃ | 30 | 200 | 64 | 24 | 39 |
| 5M HNO₃ | 30 | 600 | 65 | 60 | 35 |
| 5M HNO₃ | 60 | 200 | 68 | 62 | 32 |
| 5M HNO₃ | 60 | 600 | 68 | 91 | 30 |
| 10M HNO₃ | 5 | 200 | 68 | 32 | 35 |
| 10M HNO₃ | 5 | 600 | 68 | 70 | 24 |
| 10M HNO₃ | 30 | 200 | 72 | 65 | 39 |
| 10M HNO₃ | 30 | 600 | 72 | 83 | 34 |
| 10M HNO₃ | 60 | 200 | 75 | 72 | 34 |
| 10M HNO₃ | 60 | 600 | 77 | 95 | 35 |

The roughness measurements data demonstrates that when the implant is prepared by the methods described herein, the resulting implants contain a significantly higher roughened surface.

Surface Chemistry

Surface chemistry of the nano-modified implants was analyzed using X-ray photoelectron spectroscopy (XPS) which determines the percent of the elements on the surface and the bonding states of those elements. The titanium content of all samples, including the control implants were within the range of 73-75 weight percent with the remainder being oxygen. This demonstrates that the chemistry of the nano-modified implants is not altered when preparing the nano-modified surface of the implant.

Wettability

The surface energy results, i.e., contact angles, of the nano-modified implants are summarized in Tables 7 and 8 below. These results indicate an increase in wettability (or surface energy) when the implants are prepared by the methods described herein. Wettability of a biomaterial is important since bacteria are charged species which reside in aqueous solutions, thus, by changing the wettability of a surface, one can change bacteria adhesion and, thus, growth.

TABLE 7

Contact Angles (Wettability) of the Non-Porous Nano-Modified Implants

| Sample | Contact Angle |
|---|---|
| Non-Porous (flat) Control | 65 degrees |
| 1M $HNO_3$, 5 minutes, 200° C. | 54 degrees |
| 1M $HNO_3$, 5 minutes, 600° C. | 52 degrees |
| 1M $HNO_3$, 30 minutes, 200° C. | 53 degrees |
| 1M $HNO_3$, 30 minutes, 600° C. | 48 degrees |
| 1M $HNO_3$, 60 minutes, 200° C. | 50 degrees |
| 5M $HNO_3$, 5 minutes, 200° C. | 48 degrees |
| 5M $HNO_3$, 5 minutes, 600° C. | 47 degrees |
| 5M $HNO_3$, 30 minutes, 200° C. | 39 degrees |
| 5M $HNO_3$, 30 minutes, 600° C. | 38 degrees |
| 5M $HNO_3$, 60 minutes, 200° C. | 37 degrees |
| 5M $HNO_3$, 60 minutes, 600° C. | 35 degrees |
| 10M $HNO_3$, 5 minutes, 200° C. | 30 degrees |
| 10M $HNO_3$, 5 minutes, 600° C. | 27 degrees |
| 10M $HNO_3$, 30 minutes, 200° C. | 23 degrees |
| 10M $HNO_3$, 30 minutes, 600° C. | 20 degrees |
| 10M $HNO_3$, 60 minutes, 200° C. | 21 degrees |
| 10M $HNO_3$, 60 minutes, 600° C. | 19 degrees |

TABLE 8

Contact Angles (Wettability) of the Porous Nano-Modified Implants

| Sample | Contact Angle |
|---|---|
| Porous Control | 49 degrees |
| 1M $HNO_3$, 5 minutes, 200° C. | 38 degrees |
| 1M $HNO_3$, 5 minutes, 600° C. | 36 degrees |
| 1M $HNO_3$, 30 minutes, 200° C. | 34 degrees |
| 1M $HNO_3$, 30 minutes, 600° C. | 33 degrees |
| 1M $HNO_3$, 60 minutes, 200° C. | 30 degrees |
| 1M $HNO_3$, 60 minutes, 600° C. | 29 degrees |
| 5M $HNO_3$, 5 minutes, 200° C. | 35 degrees |
| 5M $HNO_3$, 5 minutes, 600° C. | 33 degrees |
| 5M $HNO_3$, 30 minutes, 200° C. | 30 degrees |
| 5M $HNO_3$, 30 minutes, 600° C. | 28 degrees |
| 5M $HNO_3$, 60 minutes, 200° C. | 25 degrees |
| 5M $HNO_3$, 60 minutes, 600° C. | 21 degrees |
| 10M $HNO_3$, 5 minutes, 200° C. | 29 degrees |
| 10M $HNO_3$, 5 minutes, 600° C. | 22 degrees |
| 10M $HNO_3$, 30 minutes, 200° C. | 24 degrees |
| 10M $HNO_3$, 30 minutes, 600° C. | 22 degrees |
| 10M $HNO_3$, 60 minutes, 200° C. | 15 degrees |
| 10M $HNO_3$, 60 minutes, 600° C. | 11 degrees |

Example 3

Correlation Between Material Characterization and Bacterial Adhesion

The data discussed above was plotted in graphical form in order to elucidate a correlation between material characterization (contact angle, roughness, feature width, or feature height vs. cell adhesion). Representative illustrations are demonstrated in FIGS. 20-27. Most important to note is the strong correlation between bacterial adhesion and feature width, as demonstrated in FIGS. 20-23.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of manufacturing an implant, comprising:
    a) immersing the implant in acid at a concentration of 5N to 15N for 30 minutes to 120 minutes;
    b) rinsing the acid-treated implant in an aqueous cleaner having a pH of 6 to 8 to remove the acid; and
    c) heating the rinsed implant at a temperature between 400° C. and 600° C. for about 30 minutes to about 60 minutes.

2. The method of claim 1, wherein the implant is a metal selected from the group consisting of commercially pure titanium, and titanium alloy.

3. The method of claim 1, wherein at least a portion of implant is porous prior to immersing in the acid.

4. The method of claim 1, wherein the implant is non-porous prior to immersing in the acid.

5. The method of claim 1, wherein the acid is selected from the group consisting of nitric acid, phosphoric acid, and sulfuric acid.

6. The method of claim 1, wherein the acid is nitric acid.

7. The method of claim 1, wherein the concentration of the acid is 1N to 10N.

8. The method of claim 1, wherein the implant is immersed in the acid for 30 minutes to 60 minutes.

9. The method of claim 1, wherein the implant is rinsed with deionized water.

10. The method of claim 1, wherein the implant is rinsed for 2 minutes to 10 minutes.

11. The method of claim 1, further comprising drying the rinsed implant overnight at room temperature before heating the rinsed implant to between 400° C. and 600° C.

12. The method of claim 1, wherein the temperature of the implant during heating is increased from ambient temperature to a predetermined temperature at a rate of 10° Celsius per minute.

* * * * *